(12) United States Patent
Sadegh-Nasseri

(10) Patent No.: US 8,916,340 B2
(45) Date of Patent: Dec. 23, 2014

(54) METHOD FOR IDENTIFYING AND VALIDATING DOMINANT T HELPER CELL EPITOPES USING AN HLA-DM-ASSISTED CLASS II BINDING ASSAY

(75) Inventor: Scheherazade Sadegh-Nasseri, Baltimore, MD (US)

(73) Assignee: The John Hopkins University, Baltimore, MD (US)

( * ) Notice: Subject to any disclaimer, the term of this patent is extended or adjusted under 35 U.S.C. 154(b) by 1695 days.

(21) Appl. No.: 12/160,065

(22) PCT Filed: Jan. 8, 2007

(86) PCT No.: PCT/US2007/000180
§ 371 (c)(1),
(2), (4) Date: Dec. 23, 2010

(87) PCT Pub. No.: WO2007/097828
PCT Pub. Date: Aug. 30, 2007

(65) Prior Publication Data
US 2011/0091497 A1   Apr. 21, 2011

Related U.S. Application Data

(60) Provisional application No. 60/756,882, filed on Jan. 6, 2006, provisional application No. 60/799,281, filed on May 10, 2006, provisional application No. 60/832,955, filed on Jul. 25, 2006.

(51) Int. Cl.
*C12Q 1/00* (2006.01)
*C12Q 1/37* (2006.01)
*C07K 14/74* (2006.01)
*A61K 39/385* (2006.01)

(52) U.S. Cl.
CPC .................... *C07K 14/70539* (2013.01)
USPC ................... 435/4; 435/23; 435/24; 435/68.1

(58) Field of Classification Search
None
See application file for complete search history.

(56) References Cited

FOREIGN PATENT DOCUMENTS

WO   WO-2004/031230   4/2004

OTHER PUBLICATIONS

Fernandez-Borja et al. Int. Immunol. 1996, 8(5): 625-640.*
Busch et al (FASEWB J, 2002, 16(5): A1234-A1235, abstract).*
Brehm et al (Nature Immunology, 2002, 3(7): 627-634).*
Paul (Fundamental Immunology, 2003, Philadelphia, Lippincott Williams and Wilkins, p. 623).*
van den Steen et al (FASEB J., 2002, 16: 379-389).*
Castellino et al., "Large Protein Fragments as Substrates for Endocytic Antigen Capture by MHC Class II Molecules," J. Immunology, 161:4048-4057 (1998).
Kropshofer et al., "Editing of the HLA-DR-peptide repertoire by HLA-DM," The EMBO Journal, 15(22):6144-6154 (1996).
Nanda et al., "DM Peptide-Editing Function Leads to Immunodominance in CD4 T Cell Responses In Vivo," J. Immunology, 175:6473-6480 (2005).
Vogt et al., "HLA-DM—an endosomal and lysosomal chaperone for the immune system," Trends Biochem Sci, 24(4):150-154 (1999).
International Search Report dated Sep. 24, 2007, from PCT/US2007/000180, 4 pages.

* cited by examiner

*Primary Examiner* — Gerald R Ewoldt
*Assistant Examiner* — Marianne Dibrino
(74) *Attorney, Agent, or Firm* — Foley Hoag LLP

(57) ABSTRACT

Rational design of immunotherapeutics relies on clear knowledge of the immunodominant epitopes of antigens. Current methods for identifying kinetically stable peptide-MHC complexes are in many cases inadequate for a number of reasons. Disclosed herein is a reductionistic system incorporating known participants of MHC class II antigen processing in solution to generate peptide pools from antigens, including those for which no immunodominant epitope has yet been identified, that are highly enriched for proteolytic fragments containing their immunodominant epitopes. HLA-DM-mediated editing contributes significantly to immunodominance and is exploited in discovering immunodominant epitopes from novel or previously uncharacterized antigens, particularly antigens associated with pathogens, tumors or autoimmune diseases.

11 Claims, 18 Drawing Sheets

Chain D, Crystal Structure Of Hla-Dm (SEQ ID NO: 10).
ACCESSION   2BC4_D
VERSION     2BC4_D  GI:109157211
DBSOURCE    pdb: molecule 2BC4, chain 68, release May 23, 2006;
            deposition: May 23, 2006;HLA-DM ORIGIN
        1 ggfvahvest clIddagtpk dftycisfnk dlltcwdpee nkmapcefgv lnslanvlsq
       61 hlnqkdtlmq rlrnglqnca thtqpfwgsl tnrtrppsvq vakttpfntr epvmlacyvw
      121 gfypaevtit wrkngklvmp hssahktaqp ngdwtyqtls hlaltpsygd tytcvvehig
      181 apepilrdwt pglspmqtlk kpptpppepe t LOCUS       2BC4_C                   211 aa            linear   PRI 23-MAY-2006
DEFINITION  Chain C, Crystal Structure Of Hla-Dm (SEQ ID NO: 11).
ACCESSION   2BC4_C
VERSION     2BC4_C  GI:109157210
DBSOURCE    pdb: molecule 2BC4, chain 67, release May 23, 2006;
            deposition: May 23, 2006;

ORIGIN
        1 vpeaptpmwp ddlqnhtflh tvycqdgsps vglseayded qlffffdfsqn trvprlpefa
       61 dwaqeqgdap ailfdkefce wmiqqigpkl dgkipvsrgf piaevftlkp lefgkpntlv
      121 cfvsnlfppm ltvnwqhhsv pvegfgptfv savdglsfqa fsylnftpep sdifscivth
      181 eidrytaiay wvprnalpsd lledykdddd k

Figure 10

```
LOCUS       NP_006111                261 aa
linear   PRI 17-NOV-2006
DEFINITION  major histocompatibility complex, class
II, DM alpha precursor (SEQ ID NO: 12)[Homo sapiens].
ACCESSION   NP_006111
VERSION     NP_006111.2  GI:18765715
DBSOURCE    REFSEQ: accession NM_006120.2
KEYWORDS    .
SOURCE      Homo sapiens (human)
ORIGIN      :
        1 mgheqnqgaa llqmlpllwl lphswavpea ptpmwpddlq
nhtflhtvyc qdgspsvgls
       61 eaydedqlff fdfsqntrvp rlpefadwaq eqgdapailf
dkefcewmiq qigpkldgki
      121 pvsrgfpiae vftlkplefg kpntlvcfvs nlfppmltvn
wqhhsvpveg fgptfvsavd
      181 glsfqafsyl nftpepsdif scivtheidr ytaiaywvpr
nalpsdllen vlcgvafglg
      241 vlgiivgivl iiyfrkpcsg d
//

LOCUS       NP_002109                263 aa
linear   PRI 17-NOV-2006
DEFINITION  major histocompatibility complex, class
II, DM beta precursor (SEQ ID NO: 13)[Homo sapiens].
ACCESSION   NP_002109
VERSION     NP_002109.1  GI:4504399
DBSOURCE    REFSEQ: accession NM_002118.3
KEYWORDS    .
SOURCE      Homo sapiens (human)
ORIGIN
        1 mitflplllg lslgctgagg fvahvestcl lddagtpkdf
tycisfnkdl ltcwdpeenk
       61 mapcefgvln slanvlsqhl nqkdtlmqrl rnglqncath
tqpfwgsltn rtrppsvqva
      121 kttpfntrep vmlacyvwgf ypaevtitwr kngklvmphs
sahktaqpng dwtyqtlshl
      181 altpsygdty tcvvehigap epilrdwtpg lspmqtlkvs
vsavtlglgl iifslgvisw
      241 rraghssytp lpgsnysegw his
//
```

Figure 11

```
LOCUS      NP_002115                 266 aa
linear   PRI 31-DEC-2006
DEFINITION  major histocompatibility complex, class
II, DR beta 1 precursor (SEQ ID NO: 14)[Homo
sapiens].
ACCESSION   NP_002115
VERSION     NP_002115.1  GI:4504411
DBSOURCE    REFSEQ: accession NM_002124.1
KEYWORDS    .
SOURCE      Homo sapiens (human)
ORIGIN
     1 mvclklpggs cmtaltvtlm vlssplalag dtrprflwql
kfechffngt ervrllerci
    61 ynqeesvrfd sdvgeyravt elgrpdaeyw nsqkdlleqr
raavdtycrh nygvgesftv
   121 qrrvepkvtv ypsktqplqh hnllvcsvsg fypgsievrw
frngqeekag vvstgliqng
   181 dwtfqtlvml etvprsgevy tcqvehpsvt spltvewrar
sesaqskmls gvggfvlgll
   241 flgaglfiyf rnqkghsglq ptgfls
//
```

UniProt>P01911|HB2G_HUMAN HLA class II
histocompatibility antigen, DW2.2/DR2.2 beta chain -
(SEQ ID NO: 15) Homo sapiens
GDTRPRFLWQPKRECHFFNGTERVRFLDRYFYNQEESVRFDSDVGEFRAVTEL
GRPDAEY
WNSQKDILEQARAAVDTYCRHNYGVVESFTVQRRVQPKVTVYPSKTQPLQHHN
LLVCSVS
GFYPGSIEVRWFLNGQEEKAGGVSTGLIQDDWTFQTLVMLETVPRSGEVYTCQ
VEHPSVT
SPLTVEWRARSESAQSKM

Figure 12A

```
LOCUS       NP_072049                266 aa
linear   PRI 17-NOV-2006
DEFINITION  major histocompatibility complex, class
II, DR beta 3 precursor (SEQ ID NO: 16)[Homo
sapiens].
ACCESSION   NP_072049
VERSION     NP_072049.2  GI:17986005
DBSOURCE    REFSEQ: accession NM_022555.3
KEYWORDS    .
SOURCE      Homo sapiens (human)
ORIGIN
        1 mvclklpggs slaaltvtlm vlssrlafag dtrprflelr
ksechffngt ervryldryf
       61 hnqeeflrfd sdvgeyravt elgrpvaesw nsqkdlleqk
rgrvdnycrh nygvgesftv
      121 qrrvhpqvtv ypaktqplqh hnllvcsvsg fypgsievrw
frngqeekag vvstgliqng
      181 dwtfqtlvml etvprsgevy tcqvehpsvt saltvewrar
sesaqskmls gvggfvlgll
      241 flgaglfiyf rnqkghsglq ptgfls
//
```

Figure 12B

```
LOCUS       NP_068818                266 aa
linear   PRI 18-NOV-2006
DEFINITION  major histocompatibility complex, class
II, DR beta 4 precursor (SEQ ID NO: 17) [Homo
sapiens].
ACCESSION   NP_068818 XP_945196
VERSION     NP_068818.4  GI:52630344
DBSOURCE    REFSEQ: accession NM_021983.4
KEYWORDS    .
SOURCE      Homo sapiens (human)
  1 mvclklpggs cmaaltvtlt vlssplalag dtqprfleqa
kcechflngt ervwnliryi
 61 ynqeeyaryn sdlgeyqavt elgrpdaeyw nsqkdllerr
raevdtycry nygvvesftv
121 qrrvqpkvtv ypsktqplqh hnllvcsvng fypgsievrw
frngqeekag vvstgliqng
181 dwtfqtlvml etvprsgevy tcqvehpsmm spltvqwsar
sesaqskmls gvggfvlgll
241 flgtglfiyf rnqkghsglq ptglls LOCUS       NP_002116                266 aa
linear   PRI 17-NOV-2006
DEFINITION  major histocompatibility complex, class
II, DR beta 5 precursor (SEQ ID NO: 18) [Homo
sapiens].
ACCESSION   NP_002116
VERSION     NP_002116.2  GI:18641375
DBSOURCE    REFSEQ: accession NM_002125.3
KEYWORDS    .
SOURCE      Homo sapiens (human)
ORIGIN
  1 mvclklpggs ymakltvtlm vlssplalag dtrprflqqd
kyechffngt ervrflhrdi
 61 ynqeedlrfd sdvgeyravt elgrpdaeyw nsqkdfledr
raavdtycrh nygvgesftv
121 qrrvepkvtv ypartqtlqh hnllvcsvng fypgsievrw
frnsqeekag vvstgliqng
181 dwtfqtlvml etvprsgevy tcqvehpsvt spltvewraq
sesaqskmls gvggfvlgll
241 flgaglfiyf knqkghsglh ptglvs
```

Figure 13A

UniProt>O77966|O77966_HUMAN MHC class II antigen HLA-DRB6 fragment (SEQ ID NO: 19) - Homo sapiens
QRTVYHEYRMWANSLLCRPPEGLLRAITPWCRAP UniProt>Q30217|Q30217_HUMAN MHC class II HLA-DRB9 fragment (SEQ ID NO: 20) - Homo sapiens
HFLEQIKHECYFCNGTERMRFVQRLVHTGRSMRASIGTSESSGRWRSWSGEES
RNANSQK
NLLGCLRGLLDTYCRHNYGVFESFSMHRR UniProt>P01903|2DRA_HUMAN HLA class II histocompatibility antigen, DR alpha chain precursor (SEQ ID NO: 21) - Homo sapiens
MAISGVPVLGFFIIAVLMSAQESWAIKEEHVIIQAEFYLNPDQSGEFMFDFDG
DEIFHVD
MAKKETVWRLEEFGRFASFEAQGALANIAVDKANLEIMTKRSNYTPITNVPPE
VTVLTNS
PVELREPNVLICFIDKFTPPVVNVTWLRNGKPVTTGVSETVFLPREDHLFRKF
HYLPFLP
STEDVYDCRVEHWGLDEPLLKHWEFDAPSPLPETTENVVCALGLTVGLVGIII
GTIFIIK
GVRKSNAAERRGPL

Figure 13B

SEQUENCE LISTING

<160> NUMBER OF SEQ ID NOS: 25

<210> SEQ ID NO 1
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Pro Lys Ala Val Lys Gln Asn Thr Leu Lys Leu Ala Thr
 1               5                  10

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Asp Tyr Lys Asp Asp Asp Asp Lys
 1               5

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Glu Gln Lys Leu Ile Ser Glu Glu Asp Leu
 1               5                  10

<210> SEQ ID NO 4
<211> LENGTH: 372
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Arg Gly Ser His His His His His His Thr Asp Pro Ser Ser Arg
 1               5                  10                  15

Ser Ala Asp Ala Asp Thr Ile Cys Ile Gly Tyr His Ala Asn Asn Ser
                20                  25                  30

Thr Asp Thr Val Asp Thr Val Leu Glu Lys Asn Val Thr Val Thr His
            35                  40                  45

Ser Val Asn Leu Leu Glu Asp Ser His Asn Gly Lys Leu Cys Arg Leu
        50                  55                  60

Lys Gly Ile Ala Pro Leu Gln Leu Gly Lys Cys Asn Ile Ala Gly Trp
 65                  70                  75                  80

Leu Leu Gly Asn Pro Glu Cys Asp Pro Leu Leu Pro Val Arg Ser Trp
                85                  90                  95

Ser Tyr Ile Val Glu Thr Pro Asn Ser Glu Asn Gly Ile Cys Tyr Pro
                100                 105                 110

Gly Asp Phe Ile Asp Tyr Glu Glu Leu Arg Glu Gln Leu Ser Ser Val
            115                 120                 125

```
Ser Ser Phe Glu Arg Phe Glu Ile Phe Pro Lys Glu Ser Ser Trp Pro
    130                 135                 140

Asn His Asn Thr Asn Gly Val Thr Ala Ala Cys Ser His Glu Gly Lys
145                 150                 155                 160

Ser Ser Phe Tyr Arg Asn Leu Leu Trp Leu Thr Glu Lys Glu Gly Ser
                165                 170                 175

Tyr Pro Lys Leu Lys Asn Ser Tyr Val Asn Lys Lys Gly Lys Glu Val
                180                 185                 190

Leu Val Leu Trp Gly Ile His His Pro Pro Asn Ser Lys Glu Gln Gln
            195                 200                 205

Asn Leu Tyr Gln Asn Glu Asn Ala Tyr Val Val Val Thr Ser Asn Tyr
    210                 215                 220

Asn Arg Arg Phe Phe Pro Glu Ile Ala Glu Arg Pro Lys Val Arg Asp
225                 230                 235                 240

Gln Ala Gly Arg Met Asn Tyr Tyr Trp Thr Leu Leu Lys Pro Gly Asp
                245                 250                 255

Thr Ile Ile Phe Glu Ala Asn Gly Asn Leu Ile Ala Pro Met Tyr Ala
                260                 265                 270

Phe Ala Leu Ser Arg Gly Phe Gly Ser Gly Ile Ile Thr Ser Asn Ala
            275                 280                 285

Ser Met His Glu Cys Asn Thr Lys Cys Gln Thr Pro Leu Gly Ala Ile
    290                 295                 300

Asn Ser Ser Leu Pro Tyr Gln Asn Ile His Pro Val Thr Ile Gly Glu
305                 310                 315                 320

Cys Pro Lys Tyr Val Arg Ser Ala Lys Leu Arg Met Val Thr Gly Leu
                325                 330                 335

Arg Asn Ile Pro Ser Ile Gln Ser Arg Gly Ala Cys Pro Lys Tyr Val
                340                 345                 350

Lys Gln Asn Thr Leu Lys Leu Ala Thr Gly Met Arg Lys Leu His His
            355                 360                 365

His His His His
        370

<210> SEQ ID NO 5
<211> LENGTH: 13
<212> TYPE: PRT
<213> ORGANISM: Influenza virus

<400> SEQUENCE: 5

Pro Lys Tyr Val Lys Gln Asn Thr Leu Lys Leu Ala Thr
1               5                   10

<210> SEQ ID NO 6
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: carbamidomethylcysteine

<400> SEQUENCE: 6

Gly Ala Cys Pro Lys Tyr Val Lys Gln Asn Thr Leu Lys Leu Ala Thr
1               5                   10                  15

Gly Met Arg Lys
            20
```

```
<210> SEQ ID NO 7
<211> LENGTH: 8
<212> TYPE: PRT
<213> ORGANISM: Bos sp.

<400> SEQUENCE: 7

Phe Lys Gly Glu Gln Pro Gly Lys
  1               5

<210> SEQ ID NO 8
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: Pro-OH
<220> FEATURE:
<221> NAME/KEY: MOD_RES
<222> LOCATION: (18)
<223> OTHER INFORMATION: Lys-OH
<220> FEATURE:
<221> NAME/KEY: MOD_RES
<222> LOCATION: (21)
<223> OTHER INFORMATION: Pro-OH
<220> FEATURE:
<221> NAME/KEY: MOD_RES
<222> LOCATION: (30)
<223> OTHER INFORMATION: Pro-OH

<400> SEQUENCE: 8

Gln Thr Gly Glu Pro His Gly Ile Ala Gly Phe Lys Gly Glu Gln Gly
  1               5                  10                  15

Pro Lys Gly Glu Pro Gly Pro Ala Gly Val Gln Gly Ala Pro Gly Pro
             20                  25                  30

Ala Gly

<210> SEQ ID NO 9
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)
<223> OTHER INFORMATION: Lys-OH
<220> FEATURE:
<221> NAME/KEY: MOD_RES
<222> LOCATION: (18)
<223> OTHER INFORMATION: Lys-OH
<220> FEATURE:
<221> NAME/KEY: MOD_RES
<222> LOCATION: (21)
<223> OTHER INFORMATION: Pro-OH
<220> FEATURE:
<221> NAME/KEY: MOD_RES
<222> LOCATION: (30)
<223> OTHER INFORMATION: Pro-OH

<400> SEQUENCE: 9

Gln Thr Gly Glu Pro Gly Ile Ala Gly Phe Lys His Gly Glu Gln Gly
  1               5                  10                  15

Pro Lys Gly Glu Pro Gly Pro Ala Gly Val Gln Gly Ala Pro Gly Pro
             20                  25                  30
```

Ala Gly

<210> SEQ ID NO 10
<211> LENGTH: 211
<212> TYPE: PRT
<213> ORGANISM: Homo sapiens

<400> SEQUENCE: 10

Gly Gly Phe Val Ala His Val Glu Ser Thr Cys Leu Leu Asp Asp Ala
1               5                   10                  15

Gly Thr Pro Lys Asp Phe Thr Tyr Cys Ile Ser Phe Asn Lys Asp Leu
            20                  25                  30

Leu Thr Cys Trp Asp Pro Glu Glu Asn Lys Met Ala Pro Cys Glu Phe
        35                  40                  45

Gly Val Leu Asn Ser Leu Ala Asn Val Leu Ser Gln His Leu Asn Gln
    50                  55                  60

Lys Asp Thr Leu Met Gln Arg Leu Arg Asn Gly Leu Gln Asn Cys Ala
65                  70                  75                  80

Thr His Thr Gln Pro Phe Trp Gly Ser Leu Thr Asn Arg Thr Arg Pro
                85                  90                  95

Pro Ser Val Gln Val Ala Lys Thr Thr Pro Phe Asn Thr Arg Glu Pro
            100                 105                 110

Val Met Leu Ala Cys Tyr Val Trp Gly Phe Tyr Pro Ala Glu Val Thr
        115                 120                 125

Ile Thr Trp Arg Lys Asn Gly Lys Leu Val Met Pro His Ser Ser Ala
    130                 135                 140

His Lys Thr Ala Gln Pro Asn Gly Asp Trp Thr Tyr Gln Thr Leu Ser
145                 150                 155                 160

His Leu Ala Leu Thr Pro Ser Tyr Gly Asp Thr Tyr Thr Cys Val Val
                165                 170                 175

Glu His Ile Gly Ala Pro Glu Pro Ile Leu Arg Asp Trp Thr Pro Gly
            180                 185                 190

Leu Ser Pro Met Gln Thr Leu Lys Lys Pro Thr Pro Pro Pro Pro Glu
        195                 200                 205

Pro Glu Thr
    210

<210> SEQ ID NO 11
<211> LENGTH: 211
<212> TYPE: PRT
<213> ORGANISM: Homo sapiens

<400> SEQUENCE: 11

Val Pro Glu Ala Pro Thr Pro Met Trp Pro Asp Asp Leu Gln Asn His
1               5                   10                  15

Thr Phe Leu His Thr Val Tyr Cys Gln Asp Gly Ser Pro Ser Val Gly
            20                  25                  30

Leu Ser Glu Ala Tyr Asp Glu Asp Gln Leu Phe Phe Phe Asp Phe Ser
        35                  40                  45

Gln Asn Thr Arg Val Pro Arg Leu Pro Glu Phe Ala Asp Trp Ala Gln
    50                  55                  60

Glu Gln Gly Asp Ala Pro Ala Ile Leu Phe Asp Lys Glu Phe Cys Glu
65                  70                  75                  80

Trp Met Ile Gln Gln Ile Gly Pro Lys Leu Asp Gly Lys Ile Pro Val
                85                  90                  95

```
Ser Arg Gly Phe Pro Ile Ala Glu Val Phe Thr Leu Lys Pro Leu Glu
            100                 105                 110

Phe Gly Lys Pro Asn Thr Leu Val Cys Phe Val Ser Asn Leu Phe Pro
        115                 120                 125

Pro Met Leu Thr Val Asn Trp Gln His His Ser Val Pro Val Glu Gly
    130                 135                 140

Phe Gly Pro Thr Phe Val Ser Ala Val Asp Gly Leu Ser Phe Gln Ala
145                 150                 155                 160

Phe Ser Tyr Leu Asn Phe Thr Pro Glu Pro Ser Asp Ile Phe Ser Cys
                165                 170                 175

Ile Val Thr His Glu Ile Asp Arg Tyr Thr Ala Ile Ala Tyr Trp Val
            180                 185                 190

Pro Arg Asn Ala Leu Pro Ser Asp Leu Leu Glu Asp Tyr Lys Asp Asp
        195                 200                 205

Asp Asp Lys
        210

<210> SEQ ID NO 12
<211> LENGTH: 261
<212> TYPE: PRT
<213> ORGANISM: Homo sapiens

<400> SEQUENCE: 12

Met Gly His Glu Gln Asn Gln Gly Ala Ala Leu Leu Gln Met Leu Pro
1               5                   10                  15

Leu Leu Trp Leu Leu Pro His Ser Trp Ala Val Pro Glu Ala Pro Thr
            20                  25                  30

Pro Met Trp Pro Asp Asp Leu Gln Asn His Thr Phe Leu His Thr Val
        35                  40                  45

Tyr Cys Gln Asp Gly Ser Pro Ser Val Gly Leu Ser Glu Ala Tyr Asp
    50                  55                  60

Glu Asp Gln Leu Phe Phe Phe Asp Phe Ser Gln Asn Thr Arg Val Pro
65                  70                  75                  80

Arg Leu Pro Glu Phe Ala Asp Trp Ala Gln Glu Gln Gly Asp Ala Pro
                85                  90                  95

Ala Ile Leu Phe Asp Lys Glu Phe Cys Glu Trp Met Ile Gln Gln Ile
            100                 105                 110

Gly Pro Lys Leu Asp Gly Lys Ile Pro Val Ser Arg Gly Phe Pro Ile
        115                 120                 125

Ala Glu Val Phe Thr Leu Lys Pro Leu Glu Phe Gly Lys Pro Asn Thr
    130                 135                 140

Leu Val Cys Phe Val Ser Asn Leu Phe Pro Pro Met Leu Thr Val Asn
145                 150                 155                 160

Trp Gln His His Ser Val Pro Val Glu Gly Phe Gly Pro Thr Phe Val
                165                 170                 175

Ser Ala Val Asp Gly Leu Ser Phe Gln Ala Phe Ser Tyr Leu Asn Phe
            180                 185                 190

Thr Pro Glu Pro Ser Asp Ile Phe Ser Cys Ile Val Thr His Glu Ile
        195                 200                 205

Asp Arg Tyr Thr Ala Ile Ala Tyr Trp Val Pro Arg Asn Ala Leu Pro
    210                 215                 220

Ser Asp Leu Leu Glu Asn Val Leu Cys Gly Val Ala Phe Gly Leu Gly
225                 230                 235                 240

Val Leu Gly Ile Ile Val Gly Ile Val Leu Ile Ile Tyr Phe Arg Lys
                245                 250                 255
```

Pro Cys Ser Gly Asp
            260

<210> SEQ ID NO 13
<211> LENGTH: 263
<212> TYPE: PRT
<213> ORGANISM: Homo sapiens

<400> SEQUENCE: 13

Met Ile Thr Phe Leu Pro Leu Leu Gly Leu Ser Leu Gly Cys Thr
 1               5                  10                  15

Gly Ala Gly Gly Phe Val Ala His Val Glu Ser Thr Cys Leu Leu Asp
                20                  25                  30

Asp Ala Gly Thr Pro Lys Asp Phe Thr Tyr Cys Ile Ser Phe Asn Lys
            35                  40                  45

Asp Leu Leu Thr Cys Trp Asp Pro Glu Glu Asn Lys Met Ala Pro Cys
        50                  55                  60

Glu Phe Gly Val Leu Asn Ser Leu Ala Asn Val Leu Ser Gln His Leu
 65                  70                  75                  80

Asn Gln Lys Asp Thr Leu Met Gln Arg Leu Arg Asn Gly Leu Gln Asn
                85                  90                  95

Cys Ala Thr His Thr Gln Pro Phe Trp Gly Ser Leu Thr Asn Arg Thr
            100                 105                 110

Arg Pro Pro Ser Val Gln Val Ala Lys Thr Thr Pro Phe Asn Thr Arg
        115                 120                 125

Glu Pro Val Met Leu Ala Cys Tyr Val Trp Gly Phe Tyr Pro Ala Glu
130                 135                 140

Val Thr Ile Thr Trp Arg Lys Asn Gly Lys Leu Val Met Pro His Ser
145                 150                 155                 160

Ser Ala His Lys Thr Ala Gln Pro Asn Gly Asp Trp Thr Tyr Gln Thr
                165                 170                 175

Leu Ser His Leu Ala Leu Thr Pro Ser Tyr Gly Asp Thr Tyr Thr Cys
            180                 185                 190

Val Val Glu His Ile Gly Ala Pro Glu Pro Ile Leu Arg Asp Trp Thr
        195                 200                 205

Pro Gly Leu Ser Pro Met Gln Thr Leu Lys Val Ser Val Ser Ala Val
210                 215                 220

Thr Leu Gly Leu Gly Leu Ile Ile Phe Ser Leu Gly Val Ile Ser Trp
225                 230                 235                 240

Arg Arg Ala Gly His Ser Ser Tyr Thr Pro Leu Pro Gly Ser Asn Tyr
                245                 250                 255

Ser Glu Gly Trp His Ile Ser
            260

<210> SEQ ID NO 14
<211> LENGTH: 266
<212> TYPE: PRT
<213> ORGANISM: Homo sapiens

<400> SEQUENCE: 14

Met Val Cys Leu Lys Leu Pro Gly Gly Ser Cys Met Thr Ala Leu Thr
 1               5                  10                  15

Val Thr Leu Met Val Leu Ser Ser Pro Leu Ala Leu Ala Gly Asp Thr
                20                  25                  30

Arg Pro Arg Phe Leu Trp Gln Leu Lys Phe Glu Cys His Phe Phe Asn
            35                  40                  45

```
Gly Thr Glu Arg Val Arg Leu Leu Glu Arg Cys Ile Tyr Asn Gln Glu
        50                   55                   60

Glu Ser Val Arg Phe Asp Ser Asp Val Gly Glu Tyr Arg Ala Val Thr
 65                   70                   75                   80

Glu Leu Gly Arg Pro Asp Ala Glu Tyr Trp Asn Ser Gln Lys Asp Leu
                 85                   90                   95

Leu Glu Gln Arg Arg Ala Ala Val Asp Thr Tyr Cys Arg His Asn Tyr
                100                  105                  110

Gly Val Gly Glu Ser Phe Thr Val Gln Arg Arg Val Glu Pro Lys Val
            115                  120                  125

Thr Val Tyr Pro Ser Lys Thr Gln Pro Leu Gln His His Asn Leu Leu
130                  135                  140

Val Cys Ser Val Ser Gly Phe Tyr Pro Gly Ser Ile Glu Val Arg Trp
145                  150                  155                  160

Phe Arg Asn Gly Gln Glu Glu Lys Ala Gly Val Val Ser Thr Gly Leu
                165                  170                  175

Ile Gln Asn Gly Asp Trp Thr Phe Gln Thr Leu Val Met Leu Glu Thr
                180                  185                  190

Val Pro Arg Ser Gly Glu Val Tyr Thr Cys Gln Val Glu His Pro Ser
            195                  200                  205

Val Thr Ser Pro Leu Thr Val Glu Trp Arg Ala Arg Ser Glu Ser Ala
210                  215                  220

Gln Ser Lys Met Leu Ser Gly Val Gly Gly Phe Val Leu Gly Leu Leu
225                  230                  235                  240

Phe Leu Gly Ala Gly Leu Phe Ile Tyr Phe Arg Asn Gln Lys Gly His
                245                  250                  255

Ser Gly Leu Gln Pro Thr Gly Phe Leu Ser
                260                  265

<210> SEQ ID NO 15
<211> LENGTH: 198
<212> TYPE: PRT
<213> ORGANISM: Homo sapiens

<400> SEQUENCE: 15

Gly Asp Thr Arg Pro Arg Phe Leu Trp Gln Pro Lys Arg Glu Cys His
 1               5                   10                  15

Phe Phe Asn Gly Thr Glu Arg Val Arg Phe Leu Asp Arg Tyr Phe Tyr
                20                  25                   30

Asn Gln Glu Glu Ser Val Arg Phe Asp Ser Asp Val Gly Glu Phe Arg
            35                   40                   45

Ala Val Thr Glu Leu Gly Arg Pro Asp Ala Glu Tyr Trp Asn Ser Gln
 50                   55                   60

Lys Asp Ile Leu Glu Gln Ala Arg Ala Ala Val Asp Thr Tyr Cys Arg
 65                   70                   75                   80

His Asn Tyr Gly Val Val Glu Ser Phe Thr Val Gln Arg Arg Val Gln
                 85                   90                   95

Pro Lys Val Thr Val Tyr Pro Ser Lys Thr Gln Pro Leu Gln His His
                100                  105                  110

Asn Leu Leu Val Cys Ser Val Ser Gly Phe Tyr Pro Gly Ser Ile Glu
            115                  120                  125

Val Arg Trp Phe Leu Asn Gly Gln Glu Glu Lys Ala Gly Gly Val Ser
130                  135                  140

Thr Gly Leu Ile Gln Asp Asp Trp Thr Phe Gln Thr Leu Val Met Leu
```

```
            145                 150                 155                 160
    Glu Thr Val Pro Arg Ser Gly Glu Val Tyr Thr Cys Gln Val Glu His
                    165                 170                 175
    Pro Ser Val Thr Ser Pro Leu Thr Val Glu Trp Arg Ala Arg Ser Glu
                    180                 185                 190
    Ser Ala Gln Ser Lys Met
                195

<210> SEQ ID NO 16
<211> LENGTH: 266
<212> TYPE: PRT
<213> ORGANISM: Homo sapiens

<400> SEQUENCE: 16

Met Val Cys Leu Lys Leu Pro Gly Gly Ser Ser Leu Ala Ala Leu Thr
     1               5                  10                  15
    Val Thr Leu Met Val Leu Ser Ser Arg Leu Ala Phe Ala Gly Asp Thr
                    20                  25                  30
    Arg Pro Arg Phe Leu Glu Leu Arg Lys Ser Glu Cys His Phe Phe Asn
                    35                  40                  45
    Gly Thr Glu Arg Val Arg Tyr Leu Asp Arg Tyr Phe His Asn Gln Glu
                50                  55                  60
    Glu Phe Leu Arg Phe Asp Ser Asp Val Gly Glu Tyr Arg Ala Val Thr
     65                  70                  75                  80
    Glu Leu Gly Arg Pro Val Ala Glu Ser Trp Asn Ser Gln Lys Asp Leu
                    85                  90                  95
    Leu Glu Gln Lys Arg Gly Arg Val Asp Asn Tyr Cys Arg His Asn Tyr
                    100                 105                 110
    Gly Val Gly Glu Ser Phe Thr Val Gln Arg Arg Val His Pro Gln Val
                    115                 120                 125
    Thr Val Tyr Pro Ala Lys Thr Gln Pro Leu Gln His His Asn Leu Leu
                    130                 135                 140
    Val Cys Ser Val Ser Gly Phe Tyr Pro Gly Ser Ile Glu Val Arg Trp
    145                 150                 155                 160
    Phe Arg Asn Gly Gln Glu Glu Lys Ala Gly Val Val Ser Thr Gly Leu
                    165                 170                 175
    Ile Gln Asn Gly Asp Trp Thr Phe Gln Thr Leu Val Met Leu Glu Thr
                    180                 185                 190
    Val Pro Arg Ser Gly Glu Val Tyr Thr Cys Gln Val Glu His Pro Ser
                    195                 200                 205
    Val Thr Ser Ala Leu Thr Val Glu Trp Arg Ala Arg Ser Glu Ser Ala
                    210                 215                 220
    Gln Ser Lys Met Leu Ser Gly Val Gly Gly Phe Val Leu Gly Leu Leu
    225                 230                 235                 240
    Phe Leu Gly Ala Gly Leu Phe Ile Tyr Phe Arg Asn Gln Lys Gly His
                    245                 250                 255
    Ser Gly Leu Gln Pro Thr Gly Phe Leu Ser
                    260                 265

<210> SEQ ID NO 17
<211> LENGTH: 266
<212> TYPE: PRT
<213> ORGANISM: Homo sapiens

<400> SEQUENCE: 17

Met Val Cys Leu Lys Leu Pro Gly Gly Ser Cys Met Ala Ala Leu Thr
```

```
            1               5                   10                  15
        Val Thr Leu Thr Val Leu Ser Ser Pro Leu Ala Leu Ala Gly Asp Thr
                        20                  25                  30

Gln Pro Arg Phe Leu Glu Gln Ala Lys Cys Glu Cys His Phe Leu Asn
                    35                  40                  45

Gly Thr Glu Arg Val Trp Asn Leu Ile Arg Tyr Ile Tyr Asn Gln Glu
                50                  55                  60

Glu Tyr Ala Arg Tyr Asn Ser Asp Leu Gly Glu Tyr Gln Ala Val Thr
        65                  70                  75                  80

Glu Leu Gly Arg Pro Asp Ala Glu Tyr Trp Asn Ser Gln Lys Asp Leu
                        85                  90                  95

Leu Glu Arg Arg Arg Ala Glu Val Asp Thr Tyr Cys Arg Tyr Asn Tyr
                        100                 105                 110

Gly Val Val Glu Ser Phe Thr Val Gln Arg Arg Val Gln Pro Lys Val
                        115                 120                 125

Thr Val Tyr Pro Ser Lys Thr Gln Pro Leu Gln His His Asn Leu Leu
        130                 135                 140

Val Cys Ser Val Asn Gly Phe Tyr Pro Gly Ser Ile Glu Val Arg Trp
        145                 150                 155                 160

Phe Arg Asn Gly Gln Glu Glu Lys Ala Gly Val Val Ser Thr Gly Leu
                        165                 170                 175

Ile Gln Asn Gly Asp Trp Thr Phe Gln Thr Leu Val Met Leu Glu Thr
                        180                 185                 190

Val Pro Arg Ser Gly Glu Val Tyr Thr Cys Gln Val Glu His Pro Ser
                        195                 200                 205

Met Met Ser Pro Leu Thr Val Gln Trp Ser Ala Arg Ser Glu Ser Ala
        210                 215                 220

Gln Ser Lys Met Leu Ser Gly Val Gly Gly Phe Val Leu Gly Leu Leu
        225                 230                 235                 240

Phe Leu Gly Thr Gly Leu Phe Ile Tyr Phe Arg Asn Gln Lys Gly His
                        245                 250                 255

Ser Gly Leu Gln Pro Thr Gly Leu Leu Ser
                        260                 265

<210> SEQ ID NO 18
<211> LENGTH: 266
<212> TYPE: PRT
<213> ORGANISM: Homo sapiens

<400> SEQUENCE: 18

Met Val Cys Leu Lys Leu Pro Gly Gly Ser Tyr Met Ala Lys Leu Thr
        1               5                   10                  15

Val Thr Leu Met Val Leu Ser Ser Pro Leu Ala Leu Ala Gly Asp Thr
                        20                  25                  30

Arg Pro Arg Phe Leu Gln Gln Asp Lys Tyr Glu Cys His Phe Phe Asn
                    35                  40                  45

Gly Thr Glu Arg Val Arg Phe Leu His Arg Asp Ile Tyr Asn Gln Glu
                50                  55                  60

Glu Asp Leu Arg Phe Asp Ser Asp Val Gly Glu Tyr Arg Ala Val Thr
        65                  70                  75                  80

Glu Leu Gly Arg Pro Asp Ala Glu Tyr Trp Asn Ser Gln Lys Asp Phe
                        85                  90                  95

Leu Glu Asp Arg Arg Ala Ala Val Asp Thr Tyr Cys Arg His Asn Tyr
                        100                 105                 110
```

```
Gly Val Gly Glu Ser Phe Thr Val Gln Arg Arg Val Glu Pro Lys Val
            115                 120                 125

Thr Val Tyr Pro Ala Arg Thr Gln Thr Leu Gln His His Asn Leu Leu
130                 135                 140

Val Cys Ser Val Asn Gly Phe Tyr Pro Gly Ser Ile Glu Val Arg Trp
145                 150                 155                 160

Phe Arg Asn Ser Gln Glu Glu Lys Ala Gly Val Val Ser Thr Gly Leu
                165                 170                 175

Ile Gln Asn Gly Asp Trp Thr Phe Gln Thr Leu Val Met Leu Glu Thr
            180                 185                 190

Val Pro Arg Ser Gly Glu Val Tyr Thr Cys Gln Val Glu His Pro Ser
        195                 200                 205

Val Thr Ser Pro Leu Thr Val Glu Trp Arg Ala Gln Ser Glu Ser Ala
210                 215                 220

Gln Ser Lys Met Leu Ser Gly Val Gly Gly Phe Val Leu Gly Leu Leu
225                 230                 235                 240

Phe Leu Gly Ala Gly Leu Phe Ile Tyr Phe Lys Asn Gln Lys Gly His
                245                 250                 255

Ser Gly Leu His Pro Thr Gly Leu Val Ser
            260                 265

<210> SEQ ID NO 19
<211> LENGTH: 34
<212> TYPE: PRT
<213> ORGANISM: Homo sapiens

<400> SEQUENCE: 19

Gln Arg Thr Val Tyr His Glu Tyr Arg Met Trp Ala Asn Ser Leu Leu
  1               5                  10                  15

Cys Arg Pro Pro Glu Gly Leu Leu Arg Ala Ile Thr Pro Trp Cys Arg
                20                  25                  30

Ala Pro

<210> SEQ ID NO 20
<211> LENGTH: 89
<212> TYPE: PRT
<213> ORGANISM: Homo sapiens

<400> SEQUENCE: 20

His Phe Leu Glu Gln Ile Lys His Glu Cys Tyr Phe Cys Asn Gly Thr
  1               5                  10                  15

Glu Arg Met Arg Phe Val Gln Arg Leu Val His Thr Gly Arg Ser Met
                20                  25                  30

Arg Ala Ser Ile Gly Thr Ser Glu Ser Ser Gly Arg Trp Arg Ser Trp
            35                  40                  45

Ser Gly Glu Glu Ser Arg Asn Ala Asn Ser Gln Lys Asn Leu Leu Gly
    50                  55                  60

Cys Leu Arg Gly Leu Leu Asp Thr Tyr Cys Arg His Asn Tyr Gly Val
65                  70                  75                  80

Phe Glu Ser Phe Ser Met His Arg Arg
                85

<210> SEQ ID NO 21
<211> LENGTH: 254
<212> TYPE: PRT
<213> ORGANISM: Homo sapiens

<400> SEQUENCE: 21
```

```
Met Ala Ile Ser Gly Val Pro Val Leu Gly Phe Phe Ile Ala Val
1               5                   10                  15

Leu Met Ser Ala Gln Glu Ser Trp Ala Ile Lys Glu Glu His Val Ile
            20                  25                  30

Ile Gln Ala Glu Phe Tyr Leu Asn Pro Asp Gln Ser Gly Glu Phe Met
        35                  40                  45

Phe Asp Phe Asp Gly Asp Glu Ile Phe His Val Asp Met Ala Lys Lys
    50                  55                  60

Glu Thr Val Trp Arg Leu Glu Glu Phe Gly Arg Phe Ala Ser Phe Glu
65              70                  75                  80

Ala Gln Gly Ala Leu Ala Asn Ile Ala Val Asp Lys Ala Asn Leu Glu
                85                  90                  95

Ile Met Thr Lys Arg Ser Asn Tyr Thr Pro Ile Thr Asn Val Pro Pro
            100                 105                 110

Glu Val Thr Val Leu Thr Asn Ser Pro Val Glu Leu Arg Glu Pro Asn
        115                 120                 125

Val Leu Ile Cys Phe Ile Asp Lys Phe Thr Pro Pro Val Val Asn Val
    130                 135                 140

Thr Trp Leu Arg Asn Gly Lys Pro Val Thr Thr Gly Val Ser Glu Thr
145                 150                 155                 160

Val Phe Leu Pro Arg Glu Asp His Leu Phe Arg Lys Phe His Tyr Leu
                165                 170                 175

Pro Phe Leu Pro Ser Thr Glu Asp Val Tyr Asp Cys Arg Val Glu His
            180                 185                 190

Trp Gly Leu Asp Glu Pro Leu Leu Lys His Trp Glu Phe Asp Ala Pro
        195                 200                 205

Ser Pro Leu Pro Glu Thr Thr Glu Asn Val Val Cys Ala Leu Gly Leu
    210                 215                 220

Thr Val Gly Leu Val Gly Ile Ile Gly Thr Ile Phe Ile Ile Lys
225                 230                 235                 240

Gly Val Arg Lys Ser Asn Ala Ala Glu Arg Arg Gly Pro Leu
                245                 250

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Leu Arg Met Lys Leu Pro Lys
1               5

<210> SEQ ID NO 23
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: Pro-OH
<220> FEATURE:
<221> NAME/KEY: MOD_RES
<222> LOCATION: (17)
<223> OTHER INFORMATION: Lys-OH
```

```
<220> FEATURE:
<221> NAME/KEY: MOD_RES
<222> LOCATION: (20)
<223> OTHER INFORMATION: Pro-OH
<220> FEATURE:
<221> NAME/KEY: MOD_RES
<222> LOCATION: (29)
<223> OTHER INFORMATION: Pro-OH

<400> SEQUENCE: 23

Gln Thr Gly Glu Pro Gly Ile Ala Gly Phe Lys Gly Glu Gln Gly Pro
 1               5                  10                  15

Lys Gly Glu Pro Gly Pro Ala Gly Val Gln Gly Ala Pro Gly Pro Ala
            20                  25                  30

Gly

<210> SEQ ID NO 24
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)
<223> OTHER INFORMATION: Lys-OH
<220> FEATURE:
<221> NAME/KEY: MOD_RES
<222> LOCATION: (17)
<223> OTHER INFORMATION: Lys-OH
<220> FEATURE:
<221> NAME/KEY: MOD_RES
<222> LOCATION: (20)
<223> OTHER INFORMATION: Pro-OH
<220> FEATURE:
<221> NAME/KEY: MOD_RES
<222> LOCATION: (29)
<223> OTHER INFORMATION: Pro-OH

<400> SEQUENCE: 24

Gln Thr Gly Glu Pro Gly Ile Ala Gly Phe Lys Gly Glu Gln Gly Pro
 1               5                  10                  15

Lys Gly Glu Pro Gly Pro Ala Gly Val Gln Gly Ala Pro Gly Pro Ala
            20                  25                  30

Gly

<210> SEQ ID NO 25
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 25

His His His His His His
 1               5
```

METHOD FOR IDENTIFYING AND VALIDATING DOMINANT T HELPER CELL EPITOPES USING AN HLA-DM-ASSISTED CLASS II BINDING ASSAY

RELATED APPLICATIONS

This application is a 371 national stage application of PCT/US2007/000180, filed Jan. 8, 2007, which claims priority to U.S. application Ser. No. 60/756,882, filed Jan. 6, 2006, U.S. application Ser. No. 60/799,281, filed May 10, 2006, and U.S. application Ser. No. 60/832,955, filed Jul. 25, 2006, the contents of each of which are incorporated herein by reference.

STATEMENT OF RIGHTS TO INVENTIONS MADE UNDER FEDERALLY SPONSORED RESEARCH

This invention was funded in part by grants R01GM53549 and R56AI063764 from the National Institutes of Health, which provides to the United States government certain rights in this invention.

BACKGROUND OF THE INVENTION

1. Field of the Invention

The invention in the field of biochemistry and immunology medicine relates to a method of cell-free antigen processing for MHC class II-restricted antigens that exploits the role of HLA-DM in the selection of immunodominant epitopes and permits de novo identification of immunodominant epitopes in antigens, including novel antigens for which immunodominant epitopes have not yet been identified.

2. Description of the Background Art

The ability of the immune system to focus T cell responses to a select number of epitopes potentially derivable from a complex antigen is termed "immunodominance." Several models that attempt to explain how immunodominance is established include kinetic stability for MHC binding (Lazarski, C A et al., *Immunity* 23:29-40 (2005)) and/or prevalence (Nelson, C A et al. *Proc Natl Acad Sci USA* 89:7380-3 (1992)). Other models explain immunodominance by the development of high avidity T cells recognizing those dominant peptides epitopes (Kedl, R M et al., *J Exp Med* 192:1105-13. (2000)).

For MHC class II restricted epitopes, HLA-DM ("DM"), a MHC-like molecule implicated in the editing of peptides that bind MHC II (benzin LK & Cresswell, P, *Cell* 82:155-65 (1995); Kropshofer, H. et al., *EMBO J* 15:6144-54 (1996)), may be involved in immunodominant epitope selection (Nanda N K et al., *J Exp Med* 192:781-8. (2000)). DM distinguishes its substrates (Chou C L et al., *J Exp Med* 192: 1697-1706 (2000); Belmares, M P et al., *J Immunol:*169: 5109-17 (2002); Pashine, A et al., *Immunity* 19:183-92 (2003); Stratikos, E et al., *J. Immunol.* 172:1109-17 (2004); Pu, Z et al. *Immunity* 20:467-76 (2004)) based on conformational differences between peptide/MHC complexes (Sadegh-Nasseri, S et al., *Nature* 353:167-70 (1991); Sadegh-Nasseri, S et al., *Immunol Today* 13:43-6 (1992); Sadegh-Nasseri, S et al. *Nature* 370: 647-50 (1994); Joshi, R et al., *Biochemistry* 39:3751-62 (2000)).

An empty or partially filled hydrophobic pocket 1 of HLA-DR1 constitutes a favorable substrate for DM interaction, whereas a compact and rigid conformation induced by the filling of pocket 1 (Sadegh-Nasseri, S et al., 1994, supra; 16. Stern L I et al., *Cell* 68:465-77 (1992); Natarajan, S K et al., *J. Immunol.* 162:3463-70 (1999)) is an unfavorable substrate (Chou et al., supra; Pu et al., supra).

A number of approaches have been utilized for identification of T cell epitopes that include peptide mapping, screening of synthetic peptide (or combinatorial) libraries, generation and screening of expression libraries derived from organisms or tissues of interest, and elution and sequencing of naturally occurring peptides from MHC molecules using high performance liquid chromatography (HPLC) coupled with mass spectrometry (MS). Peptide mapping and the screening of synthetic peptide libraries provide critical information, but may not identify naturally occurring ligands. Elution and sequencing methods have the advantage of providing direct information about peptide generation and MHC selection in vivo. These methods are useful in identifying cytotoxic T cell epitopes, but are less effective or ineffective in defining helper T cell epitopes, which is one of the goals of the present invention.

Examples of prior art methods for screening synthetic peptides for defining helper T cell epitopes include the following. One method is based on scanning of non-overlapping short peptides of 10-15 amino acids to encompass the entire length of a given protein. T cells from immunized individuals are the common "read-out" system for identification of the immunogenic epitopes. A major problem here is that the actual immunogenic peptide sequences may go undetected because the active region of the immunogenic peptides might not fall within the sequences chosen.

In a second approach designed to circumvent this problem, peptide sequences are designed that encompass the length of a given protein with 12-15 residue peptides of overlapping sequences. This approach although preferred, is even more tedious, costly, and often unreliable. Because of the huge number of peptides that need to be tested, and limitations on the responding T cell sources, characterization of individual peptides becomes an impossible task.

A third approach employs prediction algorithms based on MHC class II structure and the nature of eluted peptides from a given MHC protein. However, this approach relies on prediction of peptides that might bind MHC II stably but might not necessarily be immunogenic; hence this method is most unreliable.

Thus, all currently established and commonly practiced methods for identifying immunogenic epitopes are fraught with disadvantages including the fact that they are very tedious, time consuming, costly, and frequently unsuccessful. Consequently, identification of a high throughput method to isolate most likely candidate immunogenic and immunodominant epitopes derived from the natural processing of protein antigens is a most desirable goal to which the present invention is directed.

Citation of the above documents is not intended as an admission that any of the foregoing is pertinent prior art. All statements as to the date or representation as to the contents of these documents is based on the information available to the applicant and does not constitute any admission as to the correctness of the dates or contents of these documents.

SUMMARY OF THE INVENTION

The present inventors have conceived that the basis of immunodominance is the ability of peptide epitopes to form complexes with MHC H that are insensitive to DM-mediated dissociation. In other words, DM is conceived as restricting the repertoire of antigen-derived peptides that are effectively captured by MHC II molecules. This differs from the earlier notion focusing solely on stability of the peptide/MHC II complex.

The present inventors developed a new in vitro approach that incorporates the minimum number of known components of MHC II antigen presentation as soluble proteins: (a) soluble HLA-DR1, or another class II allele, such as an HLA-DR allele, such as HLA-DR1, HLA-DR2, HLA-DR3, HLA-DR4, HLA-DR5, HLA-DR6, HLA-DR7, HLA-DR8, HLA-DR9, or HLA-DR15 (or a homologue from a non-human mammalian species), or an active fragment thereof, or a sequence comprising at least 30%, 40%, 50%, 60%, 70%, 80%, 85%, 90%, 95%, 98%, or 99% sequence identity to any of the same. (b) DM, or an active fragment thereof, or a sequence comprising at least 30%, 40%, 50%, 60%, 70%, 80%, 85%, 90%, 95%, 98%, or 99% sequence identity to an allele of DM and (c) for certain embodiments, purified endosomal or lysosomal (herein "endo/lysosomal" proteases). Reactions exemplified herein were assembled under acidic conditions (pH 5.0-5.2). Cathepsins B and H are preferred enzymes as a minimal sampling of endosomal proteolytic activity because together they provide aminopeptidase and carboxypeptidase as well as endoprotease activities. (See BRENDA database, which is available on the World Wide Web at Brenda.uni-koeJn.de). Both HLA-DR1 and DM are highly resistant to digestion by the cathepsins. (See FIG. 4).

Model or test antigens were exposed to MHC binding (here, to HLA-DR1) and proteolysis after which HLA-DR1-bound peptides were isolated and analyzed (e.g., sequenced) by mass spectrometry (MS). These methods are used to identify antigenic epitopes of any protein, e.g., from a pathogenic microorganisms (bacterium, virus, etc.) of a self antigen associated with an autoimmune process or disease. Once identified, the immunodominant epitopes are used to design immunogenic compositions (or in some cases, tolerogenic compositions) such as vaccines and as correlates of immunity for immunization efficacy. Moreover, they can be used in MHC class II tetramer assays for staining specifically-activated T cells in vivo.

The present method relies on selection of a limited number of peptides actually bound to MHC class II resulting from peptide inclusion of a critical biological reagent, the DM molecule (or a non-human homologue thereof).

Non-limiting uses of the present invention include:
(1) Identification of physiologically relevant immunogenic helper T cell epitopes from any given protein, for example from any pathogen or any type of tumor or cancer cell.
(2) Epitopes identified herein can be used for vaccine preparations against pathogens, including pathogens categorized as bioterrorism agents,
(3) Cancer immunotherapy, by generating activated T cells against the relevant tumor antigens by targeting T cells to be specific for immunodominant antigens of tumor cells.
(4) Induction of immunological tolerance against antigens responsible for autoimmune diseases, many of which are caused by or associated with known protein antigens whose immunogenic and immunodominant epitopes have yet to be identified.

Thus, the present invention includes utility for both production and methods of using research reagents as well as for therapeutic, prophylactic or other clinical uses in human or veterinary medicine.

More specifically, the present invention is directed to a method for producing a complex between a polypeptide of interest comprising an immunogenic or immunodominant MHC class II restricted peptide epitope, comprising:

(a) incubating the polypeptide, optionally denatured, in the presence of
  (i) a soluble human MHC class II protein or an active homologue thereof from another mammalian species; and
  (ii) soluble human HLA-DM protein or an active homologue thereof from another mammalian species;
such that the optionally denatured polypeptide binds to the peptide binding groove of the MHC class II protein, forming a complex with the class II protein.

Also provided is a method for producing a complex between an immunogenic or immunodominant MHC class II restricted peptide from a polypeptide of interest, comprising, after step (a) above:
(b) proteolytically digesting exposed regions of the optionally denatured polypeptide so that a peptide of about 10 to about 26, preferably about 12 to about 26, more preferably 12, amino acids remains bound to the peptide binding groove of the MHC class II protein, thereby producing the complex; and Preferably, the above method further comprises, after step (b):
(c) further isolating or purifying the complex, thereby producing an isolated or purified complex.

Also provided is a method for producing an isolated immunogenic or immunodominant MHC class II restricted peptide from a polypeptide of interest, comprising producing the complex as above, and further comprising the step of:
(d) eluting or otherwise removing the peptide from the complex and isolating the peptide,
thereby producing the isolated peptide.

It is generally preferred, before step (a) to denature the polypeptide of interest to produce a denatured polypeptide that is then subjected to step (a). Polypeptides with little secondary structure (i.e., with few disulfide bonds, or an adequately long stretch of terminal residues comprising the immunodominant epitope relatively devoid of folding) may be used in the above method without an initial denaturation step.

As noted the HLA-DM molecule and the MHC class II protein may be of human origin or may be from any other mammal. The present invention is useful in both human biology and more generally, mammalian biology, and in both human and veterinary medicine.

The invention is also directed to a method for identifying or characterizing an immunogenic MHC class H restricted polypeptides of a protein, comprising isolating the peptide as above, and further comprising:
(f) identifying or characterizing the isolated peptide.

In the above method, soluble human HLA-DM protein is preferably used in step (a)(ii). In the above method, the human MHC class II protein may be a DR, DP or DQ protein, preferably DR protein. A preferred DR protein is DR1.

In the foregoing method; in step (b), the proteolytic digestion is preferably accomplished by a mixture of at least two proteinases, preferably cathepsins that occur naturally in mammalian (preferably human) endo/lysosomes. A non-limiting list of such cathepsins appears below. The at least two cathepsins may comprise cathepsin B, cathepsin H, cathepsin S or cathepsin L; more preferably cathepsin B and cathepsin H are used in this step.

In the above method, the identifying or characterizing step preferably comprises sequencing the peptide.

In the above method, the immunodominant epitope is preferably one that stimulates and/or is recognized by T helper cells. The immunodominant epitope is preferably an epitope of (i) a self antigen that is associated with or responsible for an autoimmune disease or (ii) an antigen of a pathogen or pathogenic cell. A preferred antigen of a pathogen or pathogenic cell includes, but is not limited to: a viral antigen, a bacterial antigen, a fungal antigen, a protozoal antigen, a plasmodial antigen, a helminthic antigen, and a tumor-associated antigen.

In another embodiment, the present invention is directed to a method of producing an immunogenic composition that comprises an immunogenic or immunodominant MHC class II restricted peptide from a polypeptide of interest, comprising the steps of:
  (i) producing the isolated peptide in accordance with the method described above,
  (ii) rendering the peptide into an immunogenic form; and
  (iii) optionally, adding an adjuvant or other immunostimulatory agent,
thereby producing the immunogenic composition.

The above rendering step (ii) preferably comprises coupling the peptide to an immunogenic carrier or producing a peptide multimer of at least two repeating units of the peptide. Any type of coupling or otherwise rendering a short peptide immunogenic that is know in the art may be used in this step. (For induction of tolerance rather than immunity specific for the immunodominant epitope of an antigen, any method of rendering the peptide tolerogenic known in the art may be used. This may include conjugated the peptide to a monomeric soluble carrier or one that is inherently tolerogenic, such as a self immunoglobulin (Ig) molecule, preferably IgG.)

The invention also provides a method of inducing an immune response in a host against an antigen, comprising administering to the host an effective amount of an immunogenic composition produced in accordance with the above method, wherein the peptide is an immunogenic or immunodominant epitope of the antigen. In this method, the immunodominant epitope is preferably an epitope of (i) a self antigen that is associated with or responsible for an autoimmune disease or (ii) an antigen of a pathogen or pathogenic cell. A preferred antigen of a pathogen or pathogenic cell includes, but is not limited to: a viral antigen, a bacterial antigen, a fungal antigen, a protozoal antigen, a plasmodial antigen, a helminthic antigen, and a tumor-associated antigen.

BRIEF DESCRIPTION OF THE DRAWINGS

FIG. 1a, The HA(+)DM(+) reaction. FIG. 1b, The HA(+)DM(−) reaction. FIG. 1c, The HA(−)DM(+) reaction. 100% intensity=36 mV. HLA-DR1 in FIG. 1b was pre-incubated with $HA_{Y308A}$ in PBS+0.05% azide for ~0.48 hr at 37° C. Recombinant influenza HA1 protein, HLA-DR1, DM and cathepsins B and H were assembled in reactions as described, and the resulting HLA-DR1-bound peptides were isolated and analyzed by MALDI-TOF MS. All reactions contain HLA-DR1 and cathepsins. FIG. 1d, Post-source decay (PSD) spectrum of the 2266.46 Da peak in FIG. 1a. The mass of cysteine used in the calculation of theoretical fragment masses reflects modification by iodoacetamide (added as a cathepsin inhibitor following proteolysis) into carbamidomethylcysteine. The $HA_{306-318}$ epitope is underlined.

FIG. 4a, pre-formed HA306-318/HLA-DR1 complexes were incubated in the presence or absence of 200 nM Cathepsin B and 200 nM Cathepsin H for 2 hours at 37° C. in citrate phosphate buffer pH5.2/6 mM L-cysteine/4 mM EDTA/0.05% sodium azide. Samples were pH-adjusted to pH 7.4, mixed with a modified Laemmli buffer with 0.1% SDS final concentration and no reducing agents (to maintain the integrity of the HA306-318/HLADR1 complexes), and resolved by SDS-PAGE on a 12% acrylamide gel. Samples were unboiled. Gel was silver-stained. FIG. 4b, HLA-DM was incubated with cathepsins B and H as in a. Samples were boiled for 5 min in Laemmli buffer with final concentrations of 1% SDS and 2.5% 2-mercaptoethanol, and then resolved by SDS-PAGE on a 12% acrylamide gel. Silver-stained.

FIG. 6a, 6b: Post-source decay (PSD) spectra of the 2281.77 Da species and the 2154.42 Da species in the in the HA(+)DM(+) sample in FIG. 3a. FIG. 6c: PSD spectrum of the 2281.72 Da species in the HA(+)DM(−) sample in FIG. 3b. The presence of a major PSD fragment at 64 Da less than the parent peak represents the loss of the labile $SOCH_3$ group from an oxidized methionine.

FIG. 10 depicts exemplary HLA-DM sequences for a Chain D, of HLA-DM (SEQ ID NO: 10); and Chain C, of HLA-DM (SEQ ID NO: 11).

FIG. 11 depicts exemplary HLA-DM sequences for a major histocompatibility complex, class II, DM alpha precursor (SEQ ID NO: 12) (Homo sapiens); and major histocompatibility complex, class II, DM beta precursor (SEQ ID NO: 13) (Homo sapiens).

FIG. 12 depicts exemplary DR sequences for a major histocompatibility complex, class II, DR beta 1 precursor (SEQ ID NO: 14) (Homo sapiens); human HLA class II histocompatibility antigen, DW2.21DR2.2 beta chain (SEQ ID NO: 15); and major histocompatibility complex, class II, DR beta 3 precursor (SEQ ID NO: 16)(Homo sapiens).

FIG. 13 depicts exemplary DR sequences for a major histocompatibility complex, class II, DR beta 4 precursor (SEQ ID NO: 17) (Homo sapiens); major histocompatibility complex, class II, DR beta 5 precursor (SEQ ID NO: 18) (Homo sapiens); human MHC class II antigen HLA-DRB6 fragment (SEQ ID NO: 19); human MHC class II HLA-DRB9 fragment (SEQ ID NO: 20); and 2DRA_human HLA class II histocompatibility antigen, DR alpha chain precursor (SEQ ID NO: 21).

DESCRIPTION OF THE PREFERRED EMBODIMENTS

Figure 1:
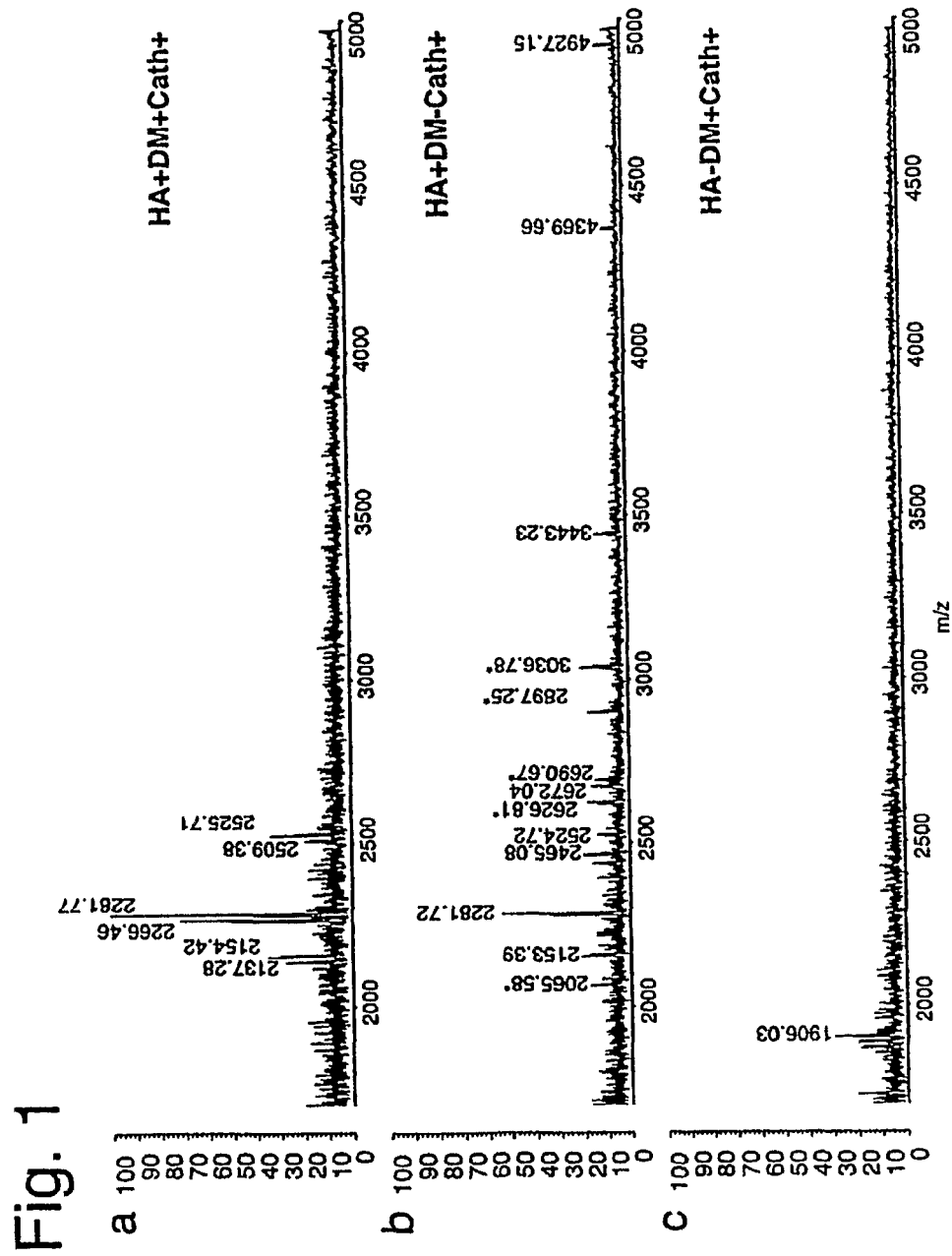
FIG. 1. MS identification of HA1-derived peptides captured by HLA-DR1.
Figure 1:
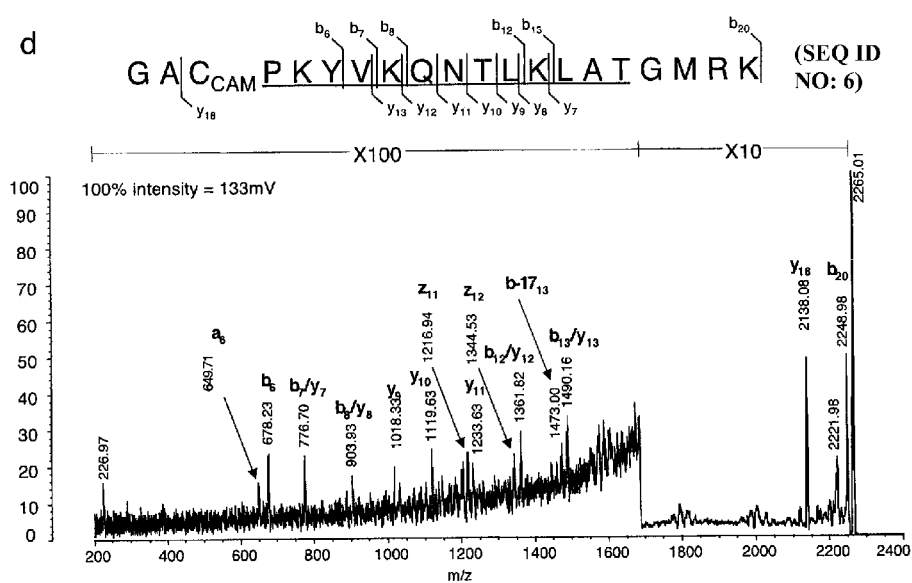

The present invention is directed to a method for identifying and validating an immunogenic, preferably an immunodominant peptide epitope which is restricted by an individual's MHC class II molecules. Such identification exploits the unique properties of the DM molecule in its interactions with MHC II and processed peptides that bind to the groove of MHC II. The methods of this invention seek to mimic the physiological process that peptides undergo when they are selected to bind to MHC H, so that a given MHC II molecule, such as an HLA-DR molecule, exemplified herein as HLA-DR1 or DR1 for short, drives the selection of the peptide. Once the peptide has bound to a DR molecule, it may be retrieved by any of a number of biochemical methods, and analyzed, sequenced, etc., so that it's identity, more importantly its amino acid sequence is known. Although the inventors have certain mechanistic explanations for the processes underlying the invention, and some of these are discussed below, the inventors do not wish to be bound by any particular model or theory of biological steps of the process when it occurs, for example, in vivo.

The method begins with a polypeptide/protein which is subjected to the method to determine the structure and sequence of the peptides that are likely to be the most immunogenic in a mammalian subject, preferably a human. Two well-known polypeptides are exemplified herein, and studied in detail. However, those skilled in the art will appreciate that this approach will work with any polypeptide.

The protein is first subject to denaturation and proteolysis to create fragments that are amenable for uptake and binding to MHC II molecules, whether they be, in the case of humans, DR, DP or DQ molecules.

Denaturation

Depending on the polypeptide, various denaturation steps well known in the art may be implemented. For example, if the polypeptide has a high content of disulfide bonds, it may be preferable to boil the protein first to break such bonds before further processing. An example of such a protein which the present inventors have studies is the L protein of human papillomavirus (HPV-L). The polypeptide may be treated, with or without boiling, with reducing agents for disulfide bonds. A preferred agent is L-cysteine at high concentrations, as exemplified herein, which interferes with S—S bond formation. Any method of denaturation can be used as long as it leaves the polypeptide in condition for the subsequent processing steps so that a peptide fragment will eventually be able to bind to MHC II and be isolated.

The polypeptide, preferably denatured, is then combined with soluble DM and DR (or, instead of DR, another MHC II molecule) and incubated for a sufficient time, preferably at least about 30 minutes at a preferred temperature of 37° C. The DM sequence may comprise HLA-DM Chain D, HLA-DM Chain C, HLA-DM alpha, or HLA-DM beta, or fragment thereof, or a sequence comprising at least 30%, 40%, 50%, 60%, 70%, 80%, 85%, 90%, 95%, 98%, or 99% sequence identity to any of the same.

Alternatively, DM may be substituted with a small molecule identified as a mimic of DM. "Small molecule" refers to a composition, which has a molecular weight of less than about 2000 kDa. Small molecules may be nucleic acids, peptides, polypeptides, peptidomimetics, carbohydrates, lipids or other organic (carbon-containing) or inorganic molecules. Non-limiting examples of small molecules that mimic DM function include peptides with the core sequence LRMKLPK (SEQ ID NO: 22).

Suitable MHC class II molecules include heterodimers of MHC class II alpha and beta subunits. Suitable alpha and beta subunits include, for example, HLA-DPalpha, HLA-DPbeta, HLA-DQalpha, HLA-DQbeta, HLA-DRalpha and HLA-DRbeta subunits. In specific embodiments, the MHC class II molecules can be, for example, DR1, DR2, DR4, DQ8, and the like. (See generally March, Tissue Antigens 51:467 (1998), incorporated hererin by reference.) The DR molecule may comprise HLA-DRB1, HLA-DRB2, HLA-DRB3, HLA-DRB4, HLA-DRB5, HLA-DRB6, HLA-DRB7, HLA-DRB8, HLA-DRB9, or HLA-DRA, or a fragment thereof, or a sequence comprising at least 30%, 40%, 50%, 60%, 70%, 80%, 85%, 90%, 95%, 98%, or 99% sequence identity to any of the same.

The MHC class II molecules are typically soluble alpha and beta polypeptides, such as the extracellular domains of the MHC class II alpha and beta subunits. Soluble forms of the MHC class II alpha and beta subunits typically include the alpha1 and alpha2 domains for the alpha subunits, and the beta1 and beta2 domains for the beta subunit, respectively. In certain embodiments, the soluble forms of the MHC class II alpha and beta subunits are the extracellular domains. Soluble alpha and beta polypeptides can be derived from the native molecules, for example, by deletion of the cytoplasmic domain and/or deletion of the transmembrane domain. Soluble MHC class II molecules can be formed by, for example, proteolytic cleavage (e.g., papain), or by genetic manipulation and expression of a genetically engineered truncated forms of the molecules.

An HLA-DM Chain D sequence may comprise SEQ ID NO: 10 (FIG. 10). An HLA-DM Chain C sequence may comprise SEQ ID NO: 11 (FIG. 10). An HLA-DM alpha sequence may comprise SEQ ID NO: 12 or a fragment thereof such as a mature peptide comprising amino acids 27-261 thereof (FIG. 11). An HLA-DM beta sequence may comprise SEQ ID NO: 13 or a fragment thereof such as a mature peptide comprising amino acids 19-263 thereof (FIG. 12). An HLA-DM sequence may comprise a fragment or a sequence comprising at least 30%, 40%, 50%, 60%, 70%, 80%, 85%, 90%, 95%, 98%, or 99% sequence identity to any of SEQ ID NOs: 10-13.

An HLA-DRB1 sequence may comprise SEQ ID NO: 14 or a fragment thereof such as a mature peptide comprising amino acids 30-266 (FIG. 12). An HLA-DRB2 sequence may comprise SEQ ID NO: 15 or a fragment thereof (FIG. 12). An HLA-DRB3 sequence may comprise SEQ ID NO: 16 or a fragment thereof such as a mature peptide comprising amino acids 30-266 thereof (FIG. 12). An HLA-DRB4 sequence may comprise SEQ ID NO: 17 or a fragment thereof such as a mature peptide comprising amino acids 30-266 thereof (FIG. 13). An HLA-DRB5 sequence may comprise SEQ ID NO: 18 or a fragment thereof such as a mature peptide comprising amino acids 30-266 thereof (FIG. 13). An HLA-DRB6 sequence may comprise SEQ ID NO: 19 or a fragment thereof (FIG. 12). An HLA-DRB9 sequence may comprise SEQ ID NO: 20 or a fragment thereof (FIG. 13). An HLA-DRA sequence may comprise SEQ ID NO: 21 or a fragment thereof (FIG. 13). An HLA-DR sequence may comprise a fragment or a sequence comprising at least 30%, 40%, 50%, 60%, 70%, 80%, 85%, 90%, 95%, 98%, or 99% sequence identity to any of SEQ ID NOs: 14-21.

In certain embodiments, the soluble forms of the alpha and beta subunits may be fusion proteins, to which additional domains can be added. Suitable domains include, for example, one or more leucine zippers, B cell (e.g., antibody) epitopes, labels, ligands for binding to a binding partner, modification sites, linker domains (e.g., a 15 to 25 amino acid peptide linker), secretion signals, and the like. For example, a leucine zipper domain can be linked to the carboxy termini of the soluble alpha and beta subunits to facilitate association of those alpha and beta subunits. Similarly, one or more linker regions can be included, such as between the soluble (extracellular) domain of an MHC class II alpha and/or beta subunits and a leucine zipper domain. The linker region typically contains polar or amphipathic amino acids to allow a flexible, unconstrained solution conformation (also referred to as a conformationally flexible linker region), in which the geometry of the MHC class II molecule, or it subunits, is unrestricted relative to other domains. Such a linker is typically about 15 to about 25 amino acids, or more, in length. A modification site, such as a BirA modification site, can also be included in or linked to the soluble alpha and/or beta subunit(s). In addition, one or more amino acids within the alpha and/or beta subunits and/or within the linker regions or the leucine zipper domains, can be substituted.

In general, preparation of MHC class II proteins, HLA-DM proteins, the polypeptide of interest, and proteolytic enzymes can be accomplished by procedures disclosed herein and by recognized recombinant DNA techniques, e.g. preparation of plasmid DNA, cleavage of DNA with restriction enzymes, ligation of DNA, transformation or transfection of a host, culturing of the host, and isolation and purification of the expressed fusion complex. Such procedures are generally known and disclosed e.g. in Sambrook, et al., Molecular Cloning (2d ed. 1989), the contents of which are incorporated herein by reference.

The soluble alpha and beta subunits may be expressed in host cells and allowed to associate to form MHC class II molecules. Alternatively, the MHC class II molecules can be formed as a single chain fusion protein of the alpha and beta subunits. For example, a single chain MEC class II molecule can be formed by linking nucleic acids encoding the soluble alpha and beta subunits in a recombinant expression cassette. Such a fusion protein can optionally include a peptide linker domain (e.g., a 15 to 25, or more, amino acid peptide linker) between the alpha and beta subunits.

In an exemplary embodiment, the MHC class subunits are formed by co-expressing nucleic acids cassettes encoding the alpha and beta subunits in host cells. One expression cassette encodes a soluble MHC class II beta subunit linked to a leucine zipper domain. A second expression cassette encodes a soluble MHC class II alpha subunit linked to a second leucine zipper domain. One of the expression cassettes typically includes a nucleic acid encoding a ligand binding domain and/or modification site. For expression, the cassettes can be inserted downstream (relative to the direction of transcription) of, and operably associated with, a promoter. The expression cassettes can be expressed from the same or different promoters.

For expression, the promoter can be selected according to the host cell. Suitable host cells include prokaryotic or eukaryotic cells, such as, for example, bacterial cells (e.g., *E. coli*, *B. subtilis*, and the like); insect cells (e.g., *Drosophila* Schneider S-2 cells); mammalian cells (e.g., CHO cells, COS cells, monkey kidney cells, lymphoid cells, and the like); fungal cells (e.g., *Saccharomyces cerevisiae*); and the like. Suitable promoters include, for example, the beta-lactamase promoter (see, e.g., VIIIa-Komaroff et. al., Proc. Natl. Acad. Sci. USA 75:3727 31 (1978)), the tac promoter (see, e.g., deBoer et al., Proc. Natl. Acad. Sci. USA 80:21 25 (1983)), or the T7 promoter for expression in *Escherichia coli*; the metallothionen promoter for expression in insect cells (see, e.g., Bunch et al., Nucleic Acids Res. 16:1043 (1988)); the SV40 early promoter region (see, e.g., Benoist and Chambon, Nature 290:304 10 (1981)), the promoter contained in the 3' long terminal repeat of Rous sarcoma virus (see, e.g., Yamamoto et al., Cell 22:787 97 (1980)), or the herpes thymidine kinase promoter (Wagner et al., Proc. Natl. Acad. Sci. USA 78:1441 45 (1981)), the regulatory sequences of the metallothionein gene (see, e.g., Brinster et al., Nature 296:39 42 (1982)) for expression in mammalian cells; the cauliflower mosaic virus 35S RNA promoter (see, e.g., Gardner et al., Nucl. Acids Res. 9:2871 88 (1981)), and the promoter of the photosynthetic enzyme ribulose biphosphate carboxylase (see, e.g., Herrera-Estrella et al., Nature 310:115 20 (1984)) for expression in plants; the Gal1 and Gal4 promoters, the alcohol dehydrogenase (ADH) promoter, and the phosphoglycerol kinase (PGK) promoter for expression in yeast; and the like.

The MHC class II subunits can also be expressed in separate host cells and the MHC class II molecules formed in vitro. Conditions that permit formation of the MHC class II subunits in vitro are known in the art (see, e.g., Arimilli et al., J Biol. Chem. 270:971 77 (1995); Altman et al., Proc. Natl. Acad. Sci. USA 90:10330 34 (1993); Garboczi et al., Proc. Natl. Acad. Sci. USA 89:3429 33 (1992); the disclosures of which are incorporated by reference herein). In one exemplary embodiment, approximately equimolar amounts of MHC class II alpha and beta subunits (e.g., MHC class II alpha and beta subunit fusion proteins) can be mixed in the presence of a denaturing agent, such as urea. The subunits can be folded by dialysis of the denaturing agent from the mixture.

The MHC class II molecules, or subunits thereof, can be purified by methods known to the skilled artisan. Such methods include for example, affinity purification (e.g., antibody, an epitope tag, and the like); column chromatography (e.g., HPLC, FPLC, and the like), and other methods. For example, to purify DQ, DR and DP MHC class II molecules, SPVL-3, L-243 and B7/27 columns, respectively, can be used. (See, e.g., Ettinger et al., J. Immunol. 165:3232 38 (2000).) In an exemplary embodiment, HLA-DR molecules are purified by affinity chromatography using monoclonal antibody L243. (See, e.g., Stern and Wiley, Cell 68:465 77 (1992); Qu and Green, DNA Cell Biol. 14:741 51 (1995).) For general guidance in suitable protein purification methods, see Scopes, Protein Purification, Springer-Verlag, New York (1982).

Without limitation, it is believed that the process works best when the MHC II molecule has just lost its "previous" peptide that was present in the groove at the time the molecule was isolated. This state is referred to as "peptide receptive" where the conformation of the peptide binding groove is open and ready to bind a new peptide. The DM protein generates or promotes this state by molecular mechanisms that are yet unknown. Without being bound by mechanism, the present inventors believe that DM causes a conformational change and breaks certain hydrogen bonds, most likely between the peptide and the P1 position in the groove of the DR molecule (such as the His $\beta^{81}$ in DR, which is an invariant position). The interaction between DM and DR is transient (and, indeed, the molecules have never been captured while bound to one another). This "hit and run" type of interaction promotes the binding of the new peptide to the MHC II groove, a type of exchange wherein the portion of the optionally denatured polypeptide being analyzed is exchanged for the peptide that previously was held in the groove. It is possible to ascertain the test polypeptide binding as a whole to DR in the presence of DM using a gel.

Proteolysis

The above mixture (optionally denatured polypeptide/MHC II/DM) is next incubated with a proteinase or, preferably, with a mixture of at least two proteinases that will remove the portions of the test polypeptide that is not held in the MHC II groove. It is preferred that the proteinases be "natural" endo/lysosomal proteinases. They should preferably have endoprotease activity and exoprotease activity from both N- and C-termini (aminopeptidase and carboxypeptidase activity). It is common that enzymes with aminopeptidase activity and those with carboxypeptidase activity also have endogenous endoprotease activity. A preferred enzyme for the present method is a cathepsin, more preferably a mixture of cathepsins. Most preferably, as exemplified herein, a mixture of cathepsins B and H are used because, together, they provide aminopeptidase and carboxypeptidase as well as endoprotease activity. The enzymes must be able to cleave the test polypeptide after it is bound to the MHC class II protein. Below is a non-limiting list of useful cathepsins. (See, for example Chapman, H A, Curr Opin Immunol 18:78-84 (2006)).

| Enzyme | Location | Cleavage type |
| --- | --- | --- |
| cathepsin B | Early endosome (E) | Carboxypeptidase |
| cathepsin X (or Z) | Early E | Carboxypeptidase |
| cathepsin S | E/lysosome | Endoprotease |
| cathepsin L (V) | Late E, lysosome | Endoprotease |
| cathepsin D | Lysosome | Endoprotease |
| cathepsin H | Lysosome | Aminopeptidase |
| cathepsin C | Early E/lysosome | Aminopeptidase |
| catheosin AEP | Lysosome | After select asparagines |

(V present in humans, not mice)

The enzyme or enzymes trim down the denatured and DR-bound test polypeptide to a physically "ideal" size in the MHC II groove. This can be as short as 10 residues, whereas 12 residues fills the groove completely, and the length may extend at both termini of the bound peptide up to a preferred total of about 26 residues.

The duration of this proteolysis step can be determined by one skilled in the art, but it is typically performed for up to about 2 hours so that proteolytic digestion is complete.

Isolation of DR-Peptide Complexes

The reaction mixture above is preferably subjected to affinity chromatography or some other method in which a DR-specific ligand, such as an anti-DR antibody, preferably an anti-DR monoclonal antibody (mAb) immobilized to a solid phase, such as beads. Alternatively, the DR molecule may be previously labeled or tagged with a tag, the presence of which does not interfere with the requisite peptide binding. Such tags are well-known to those of skill in the art. In that case, a ligand for the tag, such as a tag-specific mAb may be used to isolate the DR-peptide complex.

The bound DR-peptide complex, for example bound to beads bearing an immobilized anti-DR mAb, is washed to remove all unbound material. The DR molecules are then eluted using basic pH, for example by carbonate buffer with a pH of about 11. It is preferably to "kill" the beads, for example by crushing, so that their presence does not interfere with subsequent processing or analysis.

The peptide of interest may then be eluted from the DR protein under acid conditions, preferably at a pH of about 2-3. The peptide can then be separated from the DR protein by filtration or may be removed by size exclusion chromatography. If the elution buffer is volatile, it may be removed by vacuum drying of the peptide fraction.

Analysis of Peptide

The eluted, isolated peptide may now be analyzed by any chemical, biochemical or immunochemical means. Preferably, it is sequenced, and if the sequence of the full length polypeptide from which it was derived is known, the location of the peptide sequence in the larger polypeptide may be determined. Of course once the sequence of the peptide is known, the peptide may be synthesized using conventional techniques.

The peptide may be tested for binding with antibodies or immune sera generated using the intact polypeptide, or with T cells from animals or T cell lines with specificity for the antigen (whole polypeptide) to determine whether specificity is directed to the peptide. Such approaches will confirm the immunodominance of the peptide.

Uses of the Identified Peptide

An immunodominant peptide discovered as above may then be tested for immunogenicity in terms of the potency and breadth of an immune response by conjugating it or otherwise combining with the appropriate carrier followed by administration to a subject, preferably to a human, and measurement of the subsequence antibody or T cell response in vitro or in vivo. Those of skill in the art will know how to prepare such immunogenic forms of the peptide. Alternatively, in the case of a peptide of an autoantigen, it can be tested for its ability to induce epitope-specific tolerance and used for inducing tolerance and preventing or treating an autoimmune disease that is associated with or caused by the autoantigen. This is all within the skill in the art and requires no further inventive; effort. Reference is made to standard reference texts in immunology, such as Harlow, E. et al., *Antibodies: A Laboratory Manual*, Cold Spring Harbor Laboratory Press, Cold Spring Harbor, N.Y., 1988; Harlow, E. et al., *Using Antibodies: A Laboratory Manual: Portable Protocol NO. I*, Cold Spring Harbor Laboratory Press, Cold Spring Harbor, N.Y., 1998); A. K. Abbas et al., *Cellular and Molecular Immunology* (Fourth Ed.), W.B. Saunders Co., Philadelphia, 2000; C. A. Janeway et al., *Immunobiology. The Immune System in Health and Disease*, Fourth ed., Garland Publishing Co., New York, 1999; Roitt, I. et al., eds, *Immunology*, C. V. Mosby Co., St. Louis, Mo. (2001); Klein, J., *Immunology*, $2^{nd}$ edition, Blackwell Scientific Publications, Inc., Cambridge, Mass., (1997); Roitt, I et al., eds., *Roitt's Essential Immunology*, Blackwell Scientific Publications, Oxford (2001).

Sources of Antigens for Discovery of Immunodominant Epitopes/Peptides

Any antigenic polypeptide may be used in the present method. Preferred polypeptide are those from pathogenic viruses, bacterial, or cell (such as tumor cells) etc. An epitope of interest can be part of an antigen of a pathogenic microorganism or a toxin against which an immune response is desired. Such an epitope may be prepared directly from the antigen of interest, or alternatively, may be derived from a different antigen or toxin, but nevertheless, because of mimicry or cross-reactivity, induces an immune response to the pathogen or toxin being targeted. Non-limiting examples include a protein of a papovavirus, preferably a human papilloma virus, a rabies glycoprotein, such as glycoprotein G, a human, avian or other influenza antigen, such as turkey influenza HA, Chicken/Pennsylvania/1/83 influenza nucleoprotein (NP) antigen, an equine influenza virus antigen; a hepatitis virus antigen, such as HBsAg; a bovine leukemia virus antigen, such as gp51,30 envelope antigen; a Newcastle Disease Virus (NDV) antigen, such as HN or F; a retroviral antigen such as from an "immunodeficiency virus" such as a human immunodeficiency virus (HIV), a feline immunodeficiency virus (FIV) antigen or a simian immunodeficiency virus (SIV) antigen, or a leukemia retroviral antigen such as from feline leukemia virus (FeLV), e.g., FeLV envelope protein, an avian retroviral antigen such as from RAV, e.g., RAV-I env; a coronavirus antigen, such as matrix and/or preplomer ("spike") antigen of the SARS virus or of infectious bronchitis virus; a herpesvirus glycoprotein, such as from herpes simplex virus (HSV), cytomegalovirus (CMV), Marek's Disease Virus, feline herpesvirus, equine herpesvirus, bovine herpesvirus, pseudorabies virus, or canine herpesvirus; a flavivirus antigen, such as a from Japanese encephalitis virus (JEV), a Yellow Fever antigen, or a Dengue virus antigen; a malaria (Plasmodium) antigen, a chicken pox (varicella zoster) antigen); a parvovirus antigen, such as canine parvovirus; a poxvirus antigen, such as an ectromelia antigen, a canarypox virus antigen or a fowlpoxvirus antigen; an infectious bursal disease virus antigen, such as the proteins VP2, VP3 or VP4; a Hanta virus antigen; a mumps antigen; a Morbillivirus antigen, e.g., a canine distemper virus or measles or rinderpest antigen such as HA or F); a bacterial antigen, for example, a *Clostridium tetani* antigen, a pneumococcal antigen, such as PspA; a *Borrelia* antigen, such as OspA, OspB, OspC of *Borrelia* species associated with Lyme disease (such as *Borrelia burgdorferi, Borrelia afzelli* and *Borrelia garinii*), Of course, the foregoing lists are intended as exemplary, as the epitope of interest can be derived from any antigen of any human or veterinary pathogen.

The following references, incorporated herein by reference describe various of such antigens. *Borrelia* DNA: U.S. Pat. No. 5,523,089, WO93/08306, PCT/US92/08697, *Molecular Microbiology* (1989), 3(4): 479-486, and PCT publications WO 93/04175, and WO 96/06165; Pneumococcal epitopes: Briles et al. WO 92/14488; Tumor viruses and retroviruses: *Molecular Biology of Tumor Viruses, RNA Tumor Viruses* (Second Ed), R. Weiss et al., eds, Cold Spring Harbor Laboratory Press, 1982) (see page 44 et seq.—Taxonomy of Retroviruses), incorporated herein by reference; U.S. Pat. Nos. 5,174,993 and 5,505,941 (e.g., recombinant avipox virus, vaccinia virus, rabies glycoprotein (G), gene, turkey influenza hemagglutinin gene, gp51, 30 envelope gene of bovine leukemia virus, Newcastle Disease Virus (NDV) antigen, FeIV envelope gene, RAV-I env gene, NP (nucleoprotein gene of Chicken/Pennsylvania/1/83 influenza virus), matrix and preplomer) gene of infectious bronchitis virus, HSV gD), U.S. Pat. No. 5,338,683 discloses recombinant vaccinia virus, avipox virus, DNA encoding Herpesvirus glycoproteins, etc.; U.S. Pat. No. 5,494,807 discloses recombinant vaccinia, avipox, exogenous DNA encoding antigens from rabies, Hepatitis B, JEV, YF, Dengue, measles, pseudorabies, Epstein-Barr, HSV, HIV, SW, EHV, BHV, HCMV, canine parvovirus, equine influenza, FeLV, FHV, Hanta virus, avian influenza, mumps, NDV, etc. U.S. Pat. No. 5,503,834 discloses recombinant vaccinia, avipox, Morbillivirus, e.g., measles F, hemagglutinin, etc. U.S. Pat. No. 4,722,848 discloses recombinant vaccinia virus, HSV tk, HSV glycoproteins, e.g., gB, gD, influenza HA, Hepatitis B, e.g., HBsAg, etc. U.K. Patent GB 2269820B and U.S. Pat. No. 5,514,375 disclose recombinant poxvirus and flavivirus structural proteins. WO 92/22641 and U.S. Pat. No. 5,863,542 disclose recombinant poxvirus and immunodeficiency virus, HTLV, etc. WO 93/03145, and U.S. Pat. Nos. 5,658,572 and 5,641,490 disclose recombinant poxvirus, IBDV, etc. WO 94/16716 and U.S. Pat. No. 5,833,975 disclose recombinant poxvirus, cytokine and/or tumor associated antigens, etc. U.S. Pat. Nos. 5,529,780 and 5,688,920 disclose canine herpesviruses. WO 96/3941 and PCT/US94/06652 disclose *Plasmodium* antigens from each stage of the *Plasmodium* life cycle. See also U.S. Pat. Nos. 4,603,112, 4,769,330, 5,174,993, 5,505,941, 5,338,683, 5,494,807, 4,722,848, 5,942,335, 5,364,773, 5,762,938, 5,770,212, 5,942,235, 5,756,103, 5,766,599, 6,004,777, 5,990,091, 6,033,904, 5,869,312, 5,382,425, WO 94/16716, WO 96/39491, and documents cited therein for descriptions of various antigens and epitopes of interest the expression of which is desirable for the practice of this invention.

Vaccines

Vaccine compositions made from peptides discovered using the present method are useful in for preventing or treating diseases associated with the particular antigen, including preventing and treating infectious diseases and treating cancer. The vaccine compositions and methods are also applicable to veterinary uses.

In one embodiment, the vaccine comprises a fusion protein or peptide multimer, which includes a class II-restricted immunodominant peptide discovered or isolated as described above. The vaccine composition may further comprise an adjuvant or other immunostimulatory agent. An epitope-bearing peptide vaccine may be synthetic or produced recombinantly in prokaryotic cells or, preferably, eukaryotic cells. In view of the length of peptides isolated by the present methods, it is advantageous to couple the peptide to an immunogenic carrier to enhance its immunogenicity. Such coupling techniques are well known in the art, and include standard chemical coupling techniques using linker moieties such as those available from Pierce Chemical Company, Rockford, Ill. Suitable carriers are proteins such as keyhole limpet hemocyanin (KLH), *E. coli* pilin protein k99, BSA, or rotavirus VP6 protein.

Another vaccine embodiment is a peptide multimer (or fusion protein) which comprise the epitope-bearing peptide fused linearly to an additional amino acid sequence. Because of the ease with which recombinant materials can be manipulated, multiple copies a selected epitope-bearing region may be included in a single fusion protein molecule. Alternatively, several different epitope-bearing regions can be "mixed and matched" in a single multimer or fusion protein.

The active ingredient, or mixture of active ingredients, in protein or peptide vaccine composition is formulated conventionally using methods well-known for formulation of such vaccines. The active ingredient is generally dissolved or suspended in an acceptable carrier such as phosphate buffered saline.

Vaccine compositions may include an adjuvant or immunostimulant or may be formulated as a liposome preparation as described below. Liposomes are pharmaceutical compositions in which the active protein is contained either dispersed or variously present in corpuscles consisting of aqueous concentric layers adherent to lipidic layers. The active protein is preferably present in the aqueous layer and in the lipidic layer, inside or outside, or, in any event, in the non-homogeneous system generally known as a liposomic suspension. The hydrophobic layer, or lipidic layer, generally, but not exclusively, comprises phospholipids such as lecithin and sphingomyelin, steroids such as cholesterol, more or less ionic surface active substances such as dicetylphosphate, stearylamine or phosphatidic acid, and/or other materials of a hydrophobic nature.

The vaccine compositions preferably contain (1) an effective amount of the active ingredient, that is, the peptide together with (2) a suitable amount of a carrier molecule or, optionally a carrier vehicle, and, if desired, (3) preservatives, buffers, and the like. Descriptions of vaccine formulations are found in Voller, A. et al., *New Trends and Developments in Vaccines*, University Park Press, Baltimore, Md. (1978).

The immunogenically effective amounts of the peptide isolated by the present methods must be determined empirically. Factors to be considered include the immunogenicity of the native peptide, whether or not the peptide will be complexed with or covalently attached to an adjuvant or carrier protein or other carrier and the route of administration for the composition, i.e., intravenous, intramuscular, subcutaneous, etc., and the number of immunizing doses to be administered. Such factors are known in the vaccine art, and it is well within the skill of the immunologists to make such determinations without undue experimentation.

The vaccines are administered as is generally understood in the art. Ordinarily, systemic administration is by injection; however, other effective means of administration are known. With suitable formulation, peptide vaccines may be administered across the mucus membrane using penetrants such as bile salts or fusidic acids in combination, usually, with a surfactant. Transcutaneous administration of peptides is also known. Oral formulations can also be used. Dosage levels depend on the mode of administration, the nature of the subject, and the nature of carrier/adjuvant formulation. Preferably, an effective amount of the protein or peptide is between about 0.01 µg/kg-1 mg/kg body weight. Subjects may be immunized systemically by injection or infusion, or orally by feeding. In general, multiple administrations of the vaccine in a standard immunization protocol are used, as is standard in the art. For example, the vaccines can be administered at approximately two to six week intervals, preferably monthly, for a period of from one to four inoculations in order to provide protection.

Vaccination with the vaccine composition incorporating a peptide discovered by the present methods will result in an immune response, preferably a T helper cell response and an antibody response which will block one or more steps in a pathogenic organisms infective cycle. In the case of viruses, intracellular microorganisms, this is preferably the steps of binding to and entry into host cells in which the pathogen replicates or grows.

Adjuvants

An "adjuvant" is any substance that can be added to an immunogen or to a vaccine formulation to enhance the immune-stimulating properties of the immunogenic moiety. Liposomes are also considered to be adjuvants. See, for example, Gregoriades, G. et al., *Immunological Adjuvants and Vaccines*, Plenum Press, New York, 1989; Michalek, S. M. et al., Liposomes as Oral Adjuvants, *Curr. Top. Microbiol. Immunol.* 146:51-58 (1989).

Any immunogenic composition comprising a peptide isolated and identified as described herein may further comprise one or more adjuvants or immunostimulating agents. Examples of adjuvants or agents that may add to the effectiveness of the protein as an immunogen include aluminum hydroxide, aluminum phosphate, aluminum potassium sulfate (alum), beryllium sulfate, silica, kaolin, carbon, water-in-oil emulsions, and oil-in-water emulsions. Other adjuvants are muramyl dipeptide (MDP) and various MDP derivatives and formulations, e.g., N-acetyl-D-glucosaminyl-($\beta$1-4)-N-acetylmuramyl-L-alanyl-D-isoglutamine (GMDP) (Hornung, R L et al., *Ther Immunol* 1995 2:7-14) or ISAF-1 (5% squalene, 2.5% pluronic L121, 0.2% Tween 80 in phosphate-buffered solution with 0.4 mg of threonyl-muramyl dipeptide; see Kwak, L W et al., (1992) *N. Engl. J. Med.*, 327: 1209-1238) and monophosphoryl lipid A adjuvant solubilized in 0.02% triethanolamine. Other useful adjuvants are, or are based on, bacterial endotoxin, lipid X, whole organisms or subcellular fractions of the bacteria *Propionobacterium acnes* or *Bordetella pertussis*, polyribonucleotides, sodium alginate, lanolin, lysolecithin, vitamin A, saponin and saponin derivatives [such as QS21 (White, A. C. et al. (1991) *Adv. Exp. Med. Biol.*, 303:207-210) which is now in use in the clinic (Helling, F et al. (1995) *Cancer Res.*, 55:2783-2788; Davis, T A et al. (1997) *Blood*, 90: 509A (abstr.)], levamisole, DEAE-dextran, blocked copolymers or other synthetic adjuvants. Examples of commercially available adjuvants include (a) Amphigen®, an oil-in-water adjuvant made of de-oiled lecithin dissolved in an oil (see for example, U.S. Pat. No. 5,084,269 and US Pat Publication 20050058667A1 and (b) Alhydrogel® which is an aluminum hydroxide gel. Aluminum is approved for human use.

Adjuvants are available commercially from various sources, for example, Merck Adjuvant 65 (Merck and Company, Inc., Rahway, N.J.) or Freund's Incomplete Adjuvant and Complete Adjuvant (Difco Laboratories, Detroit, Mich.).

The immunogenic material may be adsorbed to or conjugated to beads such as latex or gold beads, ISCOMs, and the like.

Besides a classical adjuvant, the immunogenic composition may be supplemented with an immunostimulatory cytokine, lymphokine or chemokine. Preferred cytokines are GM- CSF (granulocyte-macrophage colony stimulating factor), interleukin 1, interleukin 2, interleukin 12, interleukin 18 or interferon-γ.

General methods for preparing vaccines are described, for example, in Remington's Pharmaceutical Science; Mack Publishing Company Easton, Pa. (latest edition).

Kits

The present invention provides kits comprising any of the compositions listed herein for the practice of the afore-described methods. In certain embodiments, a kit may comprise:

(i) a soluble human MHC class II protein or an active homologue thereof from another mammalian species; and (ii) a soluble human HLA-DM protein or an active homologue thereof from another mammalian species.

The soluble MHC class II protein may comprise any of the MHC class II proteins described herein, such as for example HLA-DR1, HLA-DR2, HLA-DR3, HLA-DR4, HLA-DR5, HLA-DR6, HLA-DR7, HLA-DR8, HLA-DR9, and/or HLA-DR15 or an active fragment(s) thereof, or a sequence comprising at least 30%, 40%, 50%, 60%, 70%, 80%, 85%, 90%, 95%, 98%, or 99% sequence identity to any of the same. The soluble human HLA-DM protein may comprise any of the HLA-DM proteins described herein, such as for example HLA-DM Chain D, HLA-DM Chain C, HLA-DM alpha, and/or HLA-DM beta, or an active fragment(s) thereof, or a sequence comprising at least 30%, 40%, 50%, 60%, 70%, 80%, 85%, 90%, 95%, 98%, or 99% sequence identity to any of the same.

Optionally, a kit may further comprise proteinases for digesting exposed regions of a polypeptide of interest. The proteinases may be any as described above such as, for example, cathepsin B, cathepsin H, cathepsin S, or cathepsin L, or an active fragment thereof, or a sequence comprising at least 30%, 40%, 50%, 60%, 70%, 80%, 85%, 90%, 95%, 98%, or 99% sequence identity to any of the same.

A kit may comprise a polypeptide of interest or expression vectors capable of expressing a polypeptide of interest. Optionally, a kit may comprise a library or libraries for expressing polypeptides of interest, such as for example a mammalian cDNA library derived from, for example, a mammal such as a human or mouse. In other embodiments, a kit may comprise appropriate reagents for facilitating the binding of a denatured polypeptide of interest to the peptide binding groove of the MHC class II protein, for the purpose of foming a complex of the denatured polypeptide with the said class II protein.

In lieu of providing polypeptide compositions, a kit may comprise expression vector(s) or host cells capable of harboring the expression vector(s) and for producing any of the polypeptides described above. Such a kit may comprise components for expressing the polypeptides such as buffers and reagents.

A kit may also comprise compositions for denaturing a polypeptide of interest or for identifying and purifying an immunodominant MHC class II restricted polypeptide of interest. A kit may further comprise instructions for practicing the methods described herein. Having now generally described the invention, the same will be more readily understood through reference to the following examples which are provided by way of illustration, and are not intended to be limiting of the present invention, unless specified.

EXAMPLE I

Materials and Methods

Production of Recombinant Proteins

Soluble HLA-DR1*0101 and DM were produced as described previously (Stern L I et al., *Cell* 68:465-77 (1992)) and expressed by "Hi-Five"™ cells (Invitrogen) transduced by recombinant baculovirus containing genes for the α and β chains of human HLA-DR1*0101 and DM lacking their transmembrane and cytosolic domains. The DM α and β chains were genetically modified to possess the FLAG epitope (DYKDDDDK; SEQ ID NO:2) and the cMyc epitope (EQKLISEEDL; SEQ ID NO:3), respectively, at their C-termini. Soluble DM was purified from the culture supernatant by immunoaffinity chromatography with the M2 (anti-FLAG) mAb sepharose resin (Sigma) at pH 6.0, and eluted with FLAG peptide in PBS, further purified by gel filtration chromatography (Superdex 200 HR 10/30 column, Amersham-Pharmacia).

Influenza hemagglutinin HA1 was produced in *E. coli*. Expression was induced in by the addition of 1 mM IPTG. Bacterial cells were pelleted after 5 hrs. The protein was isolated from the bacterial lysate by and affinity-purification with nickel NTA agarose (Qiagen) under denaturing conditions through the 6×His tags placed on its N- and C-termini, and refolded by stepwise dialysis into PBS. The amino acid sequence (SEQ ID NO:4) is shown below, with the $HA_{306-318}$ epitope underlined (and the two 6×His tags italicized):

```
MRGSHHHHHH TDPSSRSADA DTICIGYHAN NSTDTVDTVL

EKNVTVTHSV NLLEDSHNGK LCRLKGIAPL QLGKCNIAGW

LLGNPECDPL LPVRSWSYIV ETPNSENGIC YPGDFIDYEE

LREQLSSVSS FERFEIFPKE SSWPNHNTNG VTAACSHEGK

SSFYRNLLWL TEKEGSYPKL KNSYVNKKGK EVLVLWGIHH

PPNSKEQQNL YQNENAYVVV TSNYNRRFFP EIAERPKVRD

QAGRMNYYWT LLKPGDTIIF EANGNLIAPM YAFALSRGFG

SGIITSNASM HECNTKCQTP LGAINSSLPY QNIHPVTIGE

CPKYVRSAKL RMVTGLRNIP SIQSRGACPK YVKONTLKLA

TGMRKLHHHHHH
```

Identification of Antigen-derived Peptides Bound to HLA-DR1

Bovine type II collagen (bCII; Chondrex) was denatured and digested with MMP3-activated MMP-9 (Calbiochem). HLA-DR1, antigen and DM were incubated in citrate phosphate buffer (pH 5.0)+0.05% azide at 37° C. for ~3 hr, after which cathepsin B (bovine spleen, Sigma) and cathepsin H (human liver, Calbiochem) were added with 6 mM L-Cysteine and 4 mM EDTA for an additional ~3 hr. pH was adjusted to 7.5, 10 mM iodoacetamide was added, and HLA-DR1 was immunoprecipitated with L243 mAb-conjugated Sepharose. Bound material was eluted with 1% or 0.1% trifluoroacetic acid (TFA), incubated at room temperature for ~20 min in 1% TFA, filtered through a 10 kDa MWCO Microcon (Millipore), lyophilized, resuspended in 0.1% TFA, purified with a $C_{18}$ ZipTip® (Millipore), and analyzed on the Axima-CFR™ MALDI-TOF mass spectrometer (Kratos Analytical, Shimadzu) with data acquired in reflectron mode. The matrix used was α-cyano-4-hydroxycinnamic acid. Data analysis was accomplished with LAUNCHPAD™

(Shimadzu/Kratos Analytical) and FindPept (available on the World Wide Web at us.expasy.org/tools/findpept).

Mass Spectrometric Identification of HA-derived Peptides Captured by HLA-DR1 in the Presence of DM and Cathepsins HA was allowed to incubate with HLA-DR1 and DM prior to addition of cathepsins, thereby maximizing the likelihood of capture of the immunodominant epitope by HLA-DR1 before being potentially destroyed by cathepsins. HLA-DR1, DM, and HA protein were incubated together in citrate phosphate buffer, pH 5.2. After a 2.5 hr at 37° C., cathepsin B and cathepsin H were added, together with L-cysteine (6 mM final concentration) and EDTA (4 mM final concentration). HLA-DR1-bound peptides were isolated and analyzed as described above for bCII-derived peptides.

EXAMPLE II

Analysis of Influenza HA Protein

The influenza HA protein, a well-characterized antigen with a known HLA-DR1-restricted immunodominant epitope, was analyzed. When HLA-DR1+ individuals are infected with influenza strain A/TexasI1177, an epitope made up of residues 306-318 of the HA1 subunit ($HA_{306-318}$) having a sequence PKYVKQNTLKLAT (SEQ ID NO:5) near its C-terminus emerges as the immunodominant epitope (Lamb, J R et al., *Nature* 300:66-9 (1982)).

The present inventors used a recombinant form of HA1 derived from strain A/PR/8/34 to which the A/Texas/1/77-derived $HA_{306-318}$ epitope was (genetically) fused near the C-terminus where it is naturally present. The resulting protein, susceptible to digestion by cathepsins B and H (FIG. 5), was incubated first with HLA-DR1, with or without DM, and then with cathepsins. HLA-DR1 in the DM-free reaction was induced to adopt a peptide-receptive conformation through pre-incubation with $HAy_{308-4}$, a point mutation of the $HA_{306-318}$ peptide (Natarajan, S K et al., *J. Immunol.* 162:3463-70 (1999); Rabinowitz, J D et al., *Immunity* 9:699-709 (1998)). The association of $HAy_{308-4}$, which lacks the tyrosine crucial for the formation of a DM-resistant complex with HLA-DR1, forms a short-lived ($t_{1/2}$=34 min.) DM-sensitive complex and induces HLA-DR4 to adopt a peptide-receptive conformation in a manner similar to the influence exerted by DM (Chou C L et al., *J Exp Med* 192:1697-1706 (2000)).

Mass spectra of the resulting HLA-DR1-bound peptides are shown in FIG. 1a-1c. The HA(+)DM(+) sample contained six significant peaks (FIG. 1a). They could be separated into three pairs with members of each pair separated by 16 Da, suggesting that they reflect three unique peptides, each containing one variably oxidized methionine residue. (the sulfur in methionine is readily oxidized, causing a 16 Da mass increase).

Figure 5:
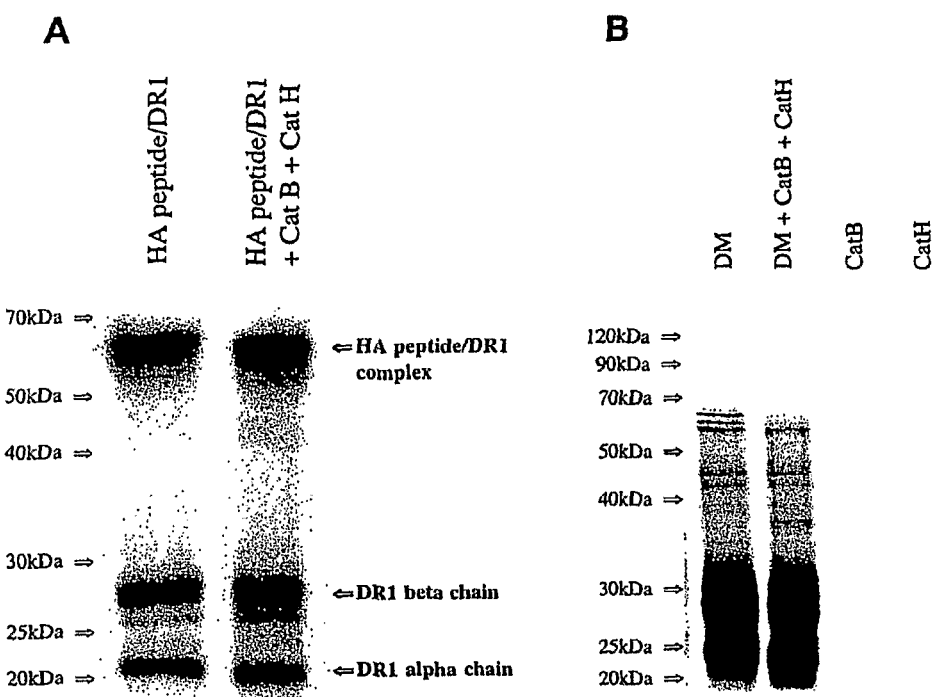
FIG. 5. HA protein is susceptible to digestion by cathepsins B and H. HA protein was incubated with cathepsins B and H (2 to 200 nM of each) in citrate phosphate buffer pH 5.2/220 mM NaCl/6 mM L-Cysteine/4 mM EDTA/7.4% sucrose/0.05% sodium azide for 2 hrs. at 37° C. The samples were mixed with standard Laemmli sample buffer and resolved by SDS-PAGE. Silver-stained.

Presence of the oxidized methionine was demonstrated for the 2282 Da and 2153 Da species through their PSD spectra (FIG. 5). The PSD spectrum of the most prominent nonoxidized species, 2266 Da, revealed fragmentation ions uniquely matching a HA1-derived peptide containing the $HA_{306-318}$ epitope (FIG. 1d, Table 1). The masses of the other species in the sample are consistent with other HA-derived peptides containing the $HA_{306-318}$ epitope.

Supportive of the present conception, the HA(+)DM(−) sample (FIG. 1b) contained many species absent in the HA(+)DM(+) sample (FIG. 1a). Those with asterisks are inconsistent in mass with any HA1-derived peptide containing the $HA_{306-318}$ epitope but are consistent with peptides derived from other portions of the protein. The mass species in the HA(+)DM(+) sample were also present in the HA(+)DM(−) sample, although only those corresponding to the methionine-oxidized forms were detected, possibly reflecting the longer duration of time that the sample was stored prior to analysis.

TABLE 1

Post-source Decay Ions of the 2266 Da Species in the HA(+)DM(+) Sample (see FIG. 1a): Comparison of Detected and Theoretical Ion Masses peptide: $GAC_{CAM}$PKYVKQNTLKLATGMRK (SEQ ID NO: 6) ($C_{CAM}$ = carbamidomethylcysteine)

| detected ions | ion type | theoretical | delta |
|---|---|---|---|
| 649.71 | a6 | 649.31 | −0.4 |
| 678.23 | b6 | 677.31 | −0.92 |
| 776.7 | b7 | 776.38 | −0.32 |
|  | y7 | 776.45 | −0.25 |
| 903.93 | b8 | 904.47 | 0.54 |
|  | y8 | 904.54 | 0.61 |
| 1018.33 | y9 | 1017.62 | −0.71 |
| 1119.63 | y10 | 1118.67 | −0.96 |
| 1216.94 | z11 | 1215.69 | −1.25 |
| 1233.63 | y11 | 1232.71 | −0.92 |
| 1344.53 | z12 | 1343.75 | −0.78 |
| 1361.61 | b12 | 1360.7 | −0.91 |
|  | y12 | 1360.77 | −0.84 |
| 1473 | b-17 13 | 1471.8 | −1.2 |
| 1490.16 | b13 | 1488.8 | −1.36 |
|  | y13 | 1488.87 | −1.29 |
| 2138.08 | y18 | 2136.18 | −1.9 |
| 2248.98 | b20 | 2246.23 | −2.75 |
| 2265.01 | parent | 2264.24 | −0.77 |

EXAMPLE III

Analysis of Type II Collagen

The present system was next applied to type II collagen (CII), the suspected autoantigen in rheumatoid arthritis (RA) (Trentham, D E et al., *J Exp Med* 146:857-68 (1977); Yoo, T J et al., *J Exp Med* 168:777-82 (1988)) The DR1-restricted immunodominant epitope of CII is known to be comprised of residues 282-289, FKGEQPGK (SEQ ID NO:7) (Rosloniec, E F et al., *J. Immunol.* 160:2573-8 (1998)). Bovine CII was used because it is 98% identical in sequence with human CII and the $CII_{282-289}$ epitope is conserved.

Figure 6:
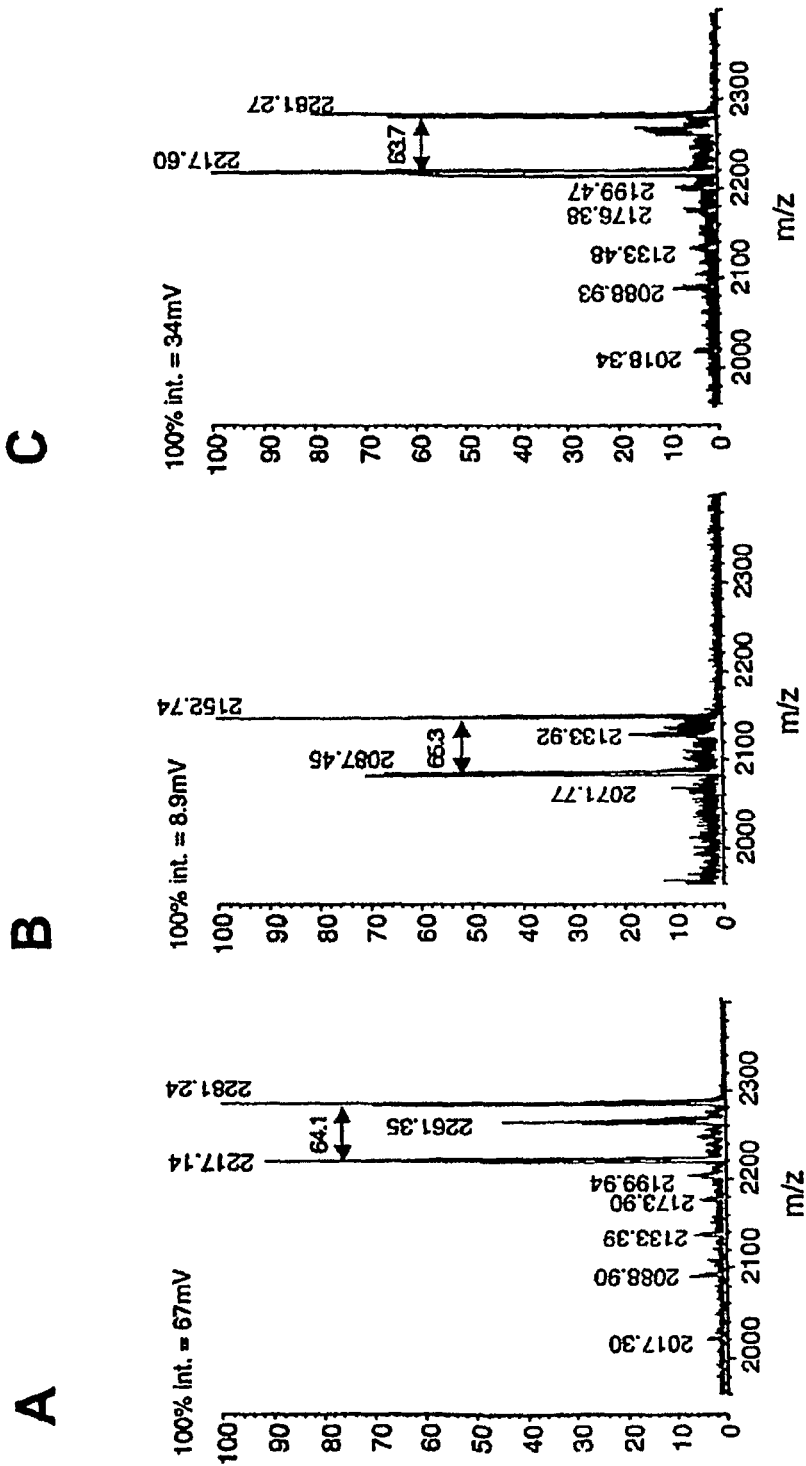
FIG. 6. HA-derived peptides contain an oxidized methionine.
Figure 7:
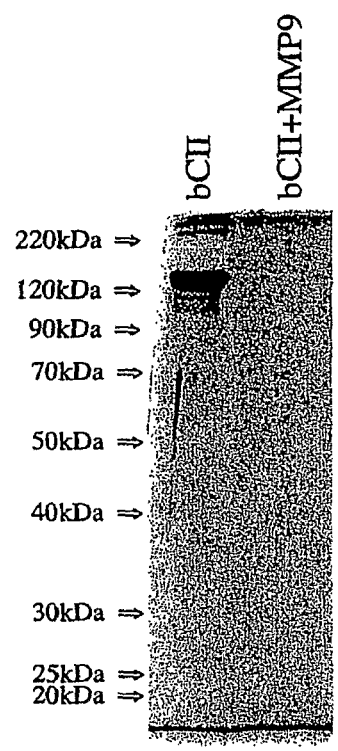
FIG. 7. Digestion of denatured bovine type II collagen with MMP9. 6.6 µM denatured bovine type II collagen (bCII) was incubated with or without 6.5 nM matrix metalloproteinase 9 (MMP9) at 37° C. for 4 hr in MMP9 reaction buffer: 100 mM Tris-HCl pH 7.5, 100 mM NaCl, 10 mM $CaCl_2$, 0.01% Tween 20 and 0.05% sodium azide. Samples were resolved by SDS-PAGE on a 12% acrylamide gel. Silver stained.
Figure 8:
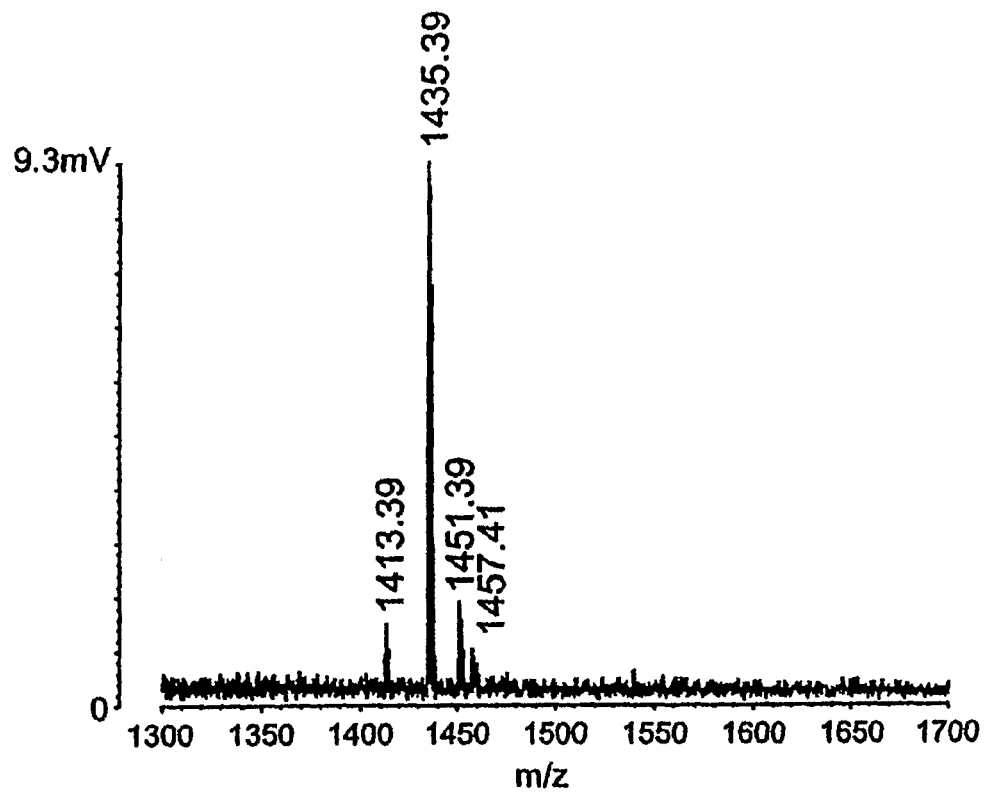
FIG. 8. Partial mass spectrum of peptides eluted from HLA-DR1 after incubation with MMP9-digested HLA-DR1 in the presence of DM, without the addition of cathepsins B and H. Here, HLA-DR1 was not preloaded with the $HA_{Y308.4}$ peptide (PKAVKQNTLKLAT, SEQ ID NO:1, averaged mass=1411.70) prior to use in the experiment. Note that the ~1413 Da and ~1435 Da mass species are still present.

Bovine CII (bCII) was digested with matrix metalloproteinase (MMP) 9 (FIG. 6), a neutrophil protease suspected of generating immunologically active CII fragments in RA and known to leave the $CII_{282-289}$ epitope intact (Van den Steen, P E et al., *FASEB J* 16:379-89 (2002); Van den Steen, P E et al., *Biochemistry* 43:10809-16 (2004)).

Figure 2A:
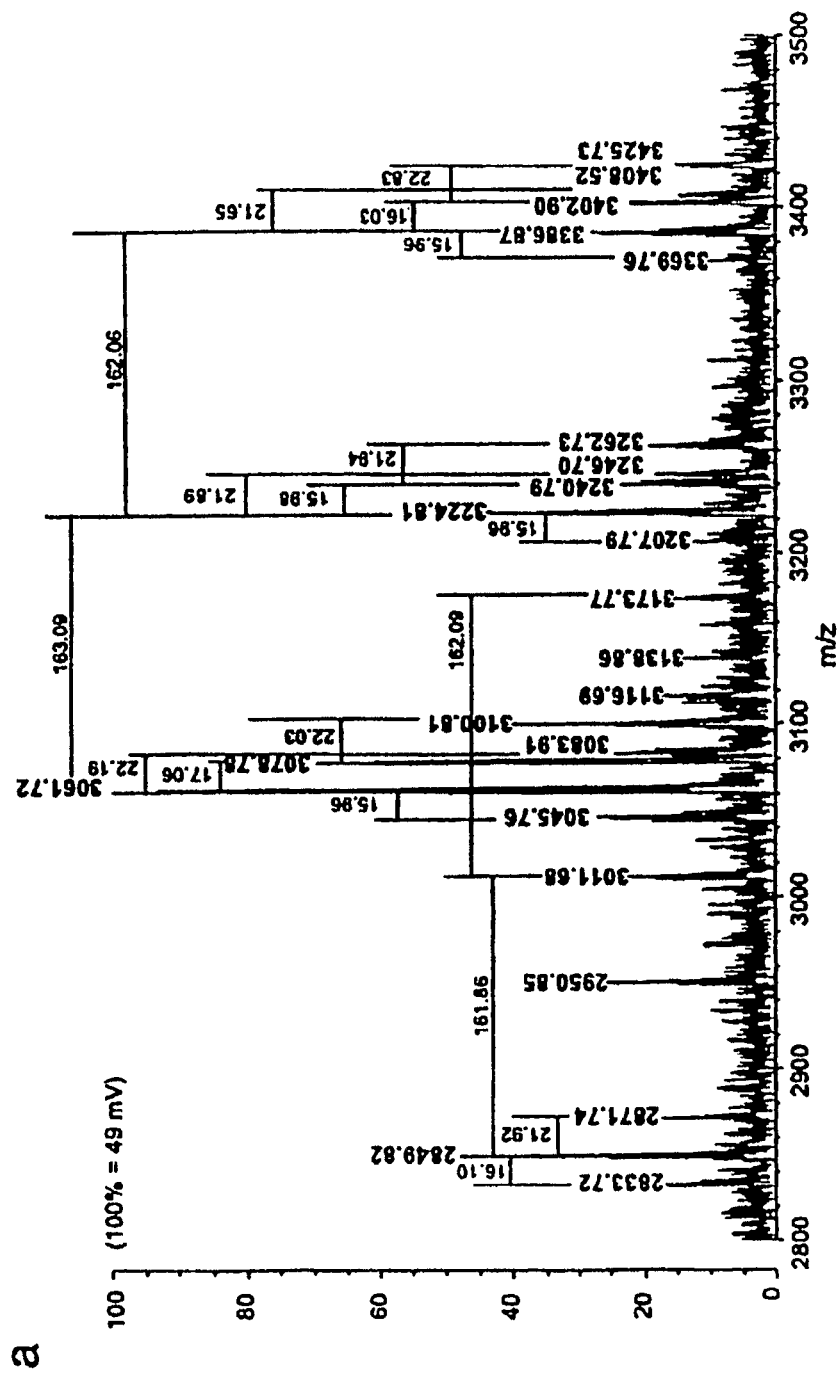
FIG. 2. MS identification of bCII-derived peptides captured by HLA-DR1. a, The primary cluster of peaks in the mass spectrum of peptides eluted from HLA-DR1 after incubation with MMP9-digested bovine type II collagen (bCII) in the presence of DM, followed by digestion with cathepsins B and H. CII possesses hydroxylysines and hydroxyprolines as well as hexose-glycosylated hydroxylysines (Van den Steen, P E et al., *FASEB J* 16:379-89 (2002); Van den Steen, P E et al., *Biochemistry* 43:10809-16 (2004)). Hydroxylation=+16 Da. Sodiation=+22 mV. Hexose=162 Da.
FIG. 2b: The post-source decay (PSD) spectrum of the 3061.72 Da peak in FIG. 2a is consistent with a non-glycosylated form of $bCII_{273-305}$ with two possible patterns of four hydroxylations. PSD ions found only in the top hydroxylation variant are shown in bold; all other ions are found in both variants. The $CII_{282-289}$ epitope is underlined.
FIGS. 2c and 2d: PSD spectra of the 3224.81 Da and 3386.87 Da peaks seen in a, revealing the presence of one and two hexoses respectively.
Figure 2:
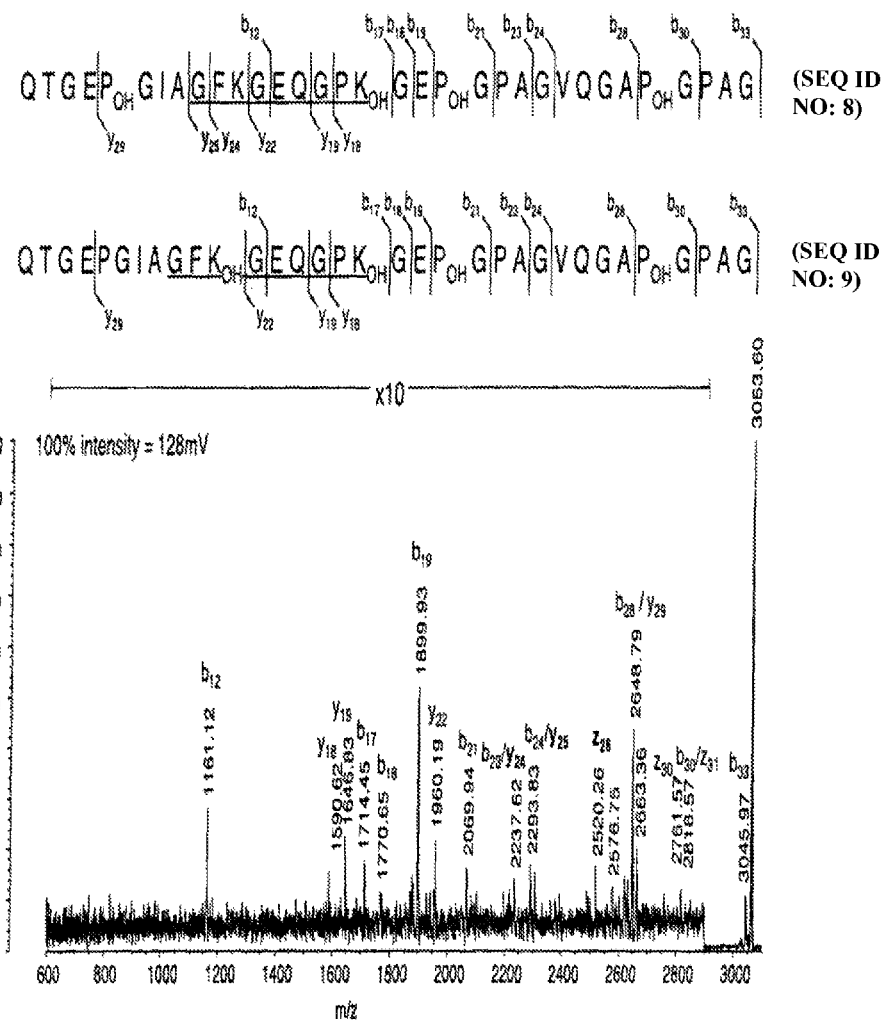
Figure 2:
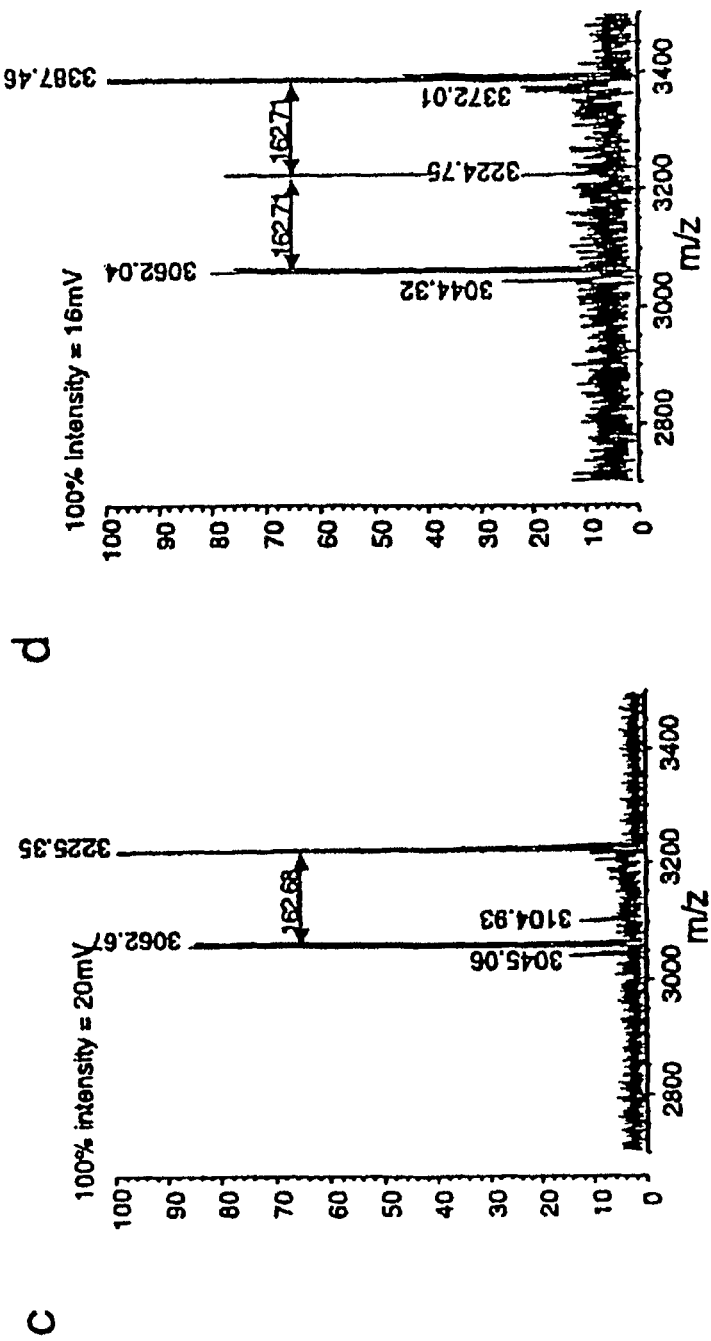
Figure 3:
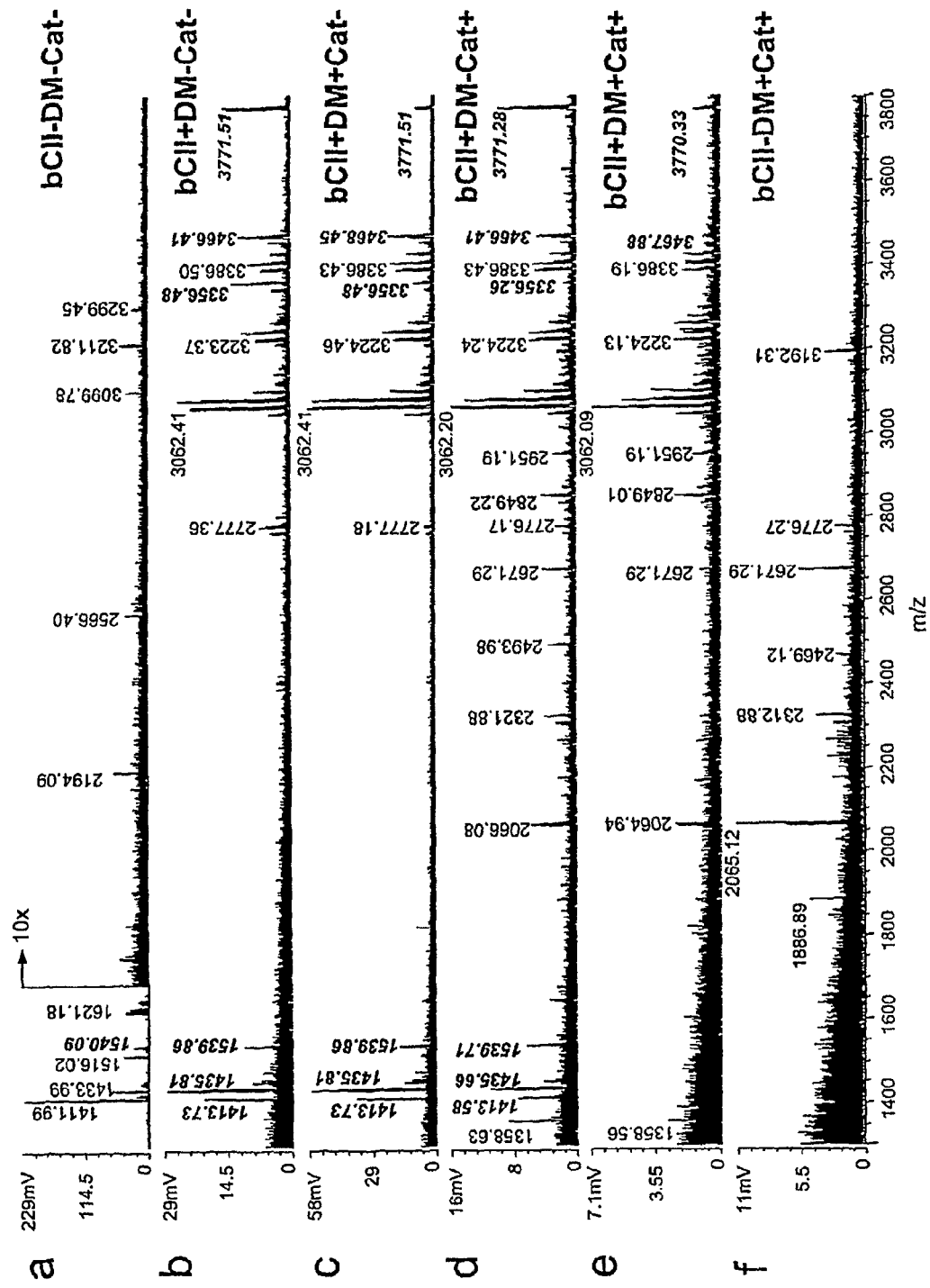
FIG. 3. HLA-DM and cathepsins synergistically restrict the repertoire of bCII-derived peptides captured by HLA-DR1. Peptides captured by HLA-DR1 in reactions containing HLA-DR1 alone (FIG. 3a), MMP9-digested bovine type II collagen (bCII×MMP9) (FIG. 3b), bCII×MMP9 and DM (FIG. 3c), bCII×MMP9 with cathepsins B and H (FIG. 3d), bCII×MMP9 and DM with cathepsins B and H (FIG. 3e), and HLA-DR1 and DM alone with cathepsins B and H (FIG. 3f). HLA-DR1 in all reactions was pre-incubated with $HA_{Y308A}$. Mass species present in FIG. 3b but absent (or significantly reduced) in FIG. 3e are labeled in bold italics. The 1411.99 Da and 1433.99 species in FIG. 3a are $HA_{Y308A}$ and its sodium adduct (averaged masses: 1411.70 and 1433.70, respectively). The 1413 Da and 1435 Da species appearing in FIGS. 3b-d are bCII-derived species whose masses do not overlap with those of $HA_{Y308A}$ and its sodium adduct. They are absent in FIG. 3a, and are present in a $HA_{Y308A}$-free reaction equivalent to FIG. 3c (see FIG. 8).
Figure 4:
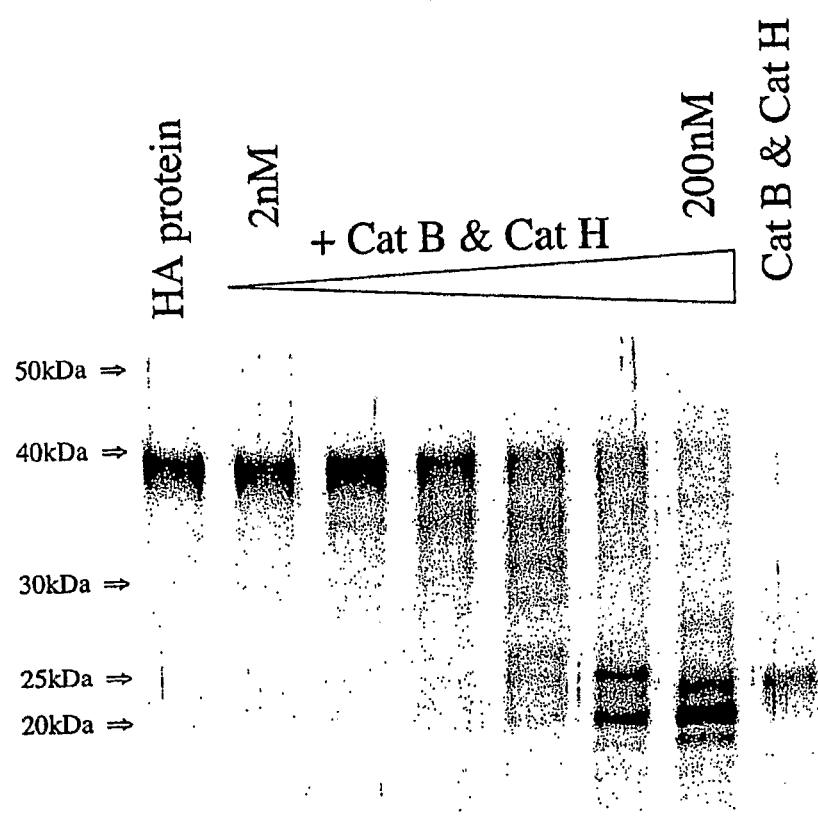
FIG. 4. HLA-DR1 and HLA-DM are resistant to Cathepsins B and H.

The bCII fragments were incubated with HLA-DR1, with or without DM, and were then incubated with or without cathepsins. When both DM and cathepsins were present, most of the peptides eluted from HLA-DR1 fell within a single cluster between 3000 Da and 3500 Da (FIGS. 2a, and 3e).

Based on the post-translational modifications (PTM's) that CII possesses (Van den Steen, 2202, 2004, supra) almost all of the species in this cluster are consistent with being PTM variants of one peptide. The PSD fragmentation of the most prominent species, 3063 Da, revealed its identity to be bCII residues 273-305, which contains the bCII$_{282-289}$ epitope (FIG. 2b; Table 2). The putative monohexose and dihexose glycosylated forms of this fragment were also confirmed though PSD analysis (FIG. 2c, d), and are consistent with the known glycosylations of the lysines within bCII$_{282-289}$ (Van den Steen, 2202, 2004, supra). The appearance of this cluster even in the absence of cathepsins (FIG. 3b, c), indicating that bCII$_{273-305}$ is generated by MMP9 alone, is consistent with the known MMP9 cleavage sites within bCII (Van den Steen, P E et al., *Biochemistry* 43:10809-16 (2004)). The 2850 Da species, appearing only upon the addition of cathepsins (FIG. 3d, e), is consistent with an N-terminal trimmed form of the 3063 Da species, bCII$_{275-305}$, in terms of both its mass and the presence of the expected putative glycosylations and hydroxylations (FIG. 2a).

When cathepsins are present, the DM(−) sample (FIG. 3d) contains many species in addition to those present in the DM(+) sample (FIG. 3e), thus confirming our hypothesis that DM restricts the repertoire of peptides captured by HLA-DR1. The lack of detectable glycosylation variants among the DM-sensitive species indicates that they are derived from regions of bCII not containing the bCII$_{282-289}$ epitope. However, when cathepsins are absent, the peptide repertoires of the DM(−) and DM(+) samples are nearly identical (FIG. 3b, c). The inability of DM to restrict the peptide repertoire in the absence of proteolytic activity can be explained by the dual nature of DM's influence on peptide-MHC II interaction. While DM selectively enhances peptide/MHC II dissociation depending on whether the peptide induces the MHC II to adopt a DM-sensitive conformation, DM globally enhances peptide-MHC II association by maintaining unoccupied MEC II molecules in a peptide-receptive conformation. The presence of DM would thus cause both an increase in the dissociation rate of DM-sensitive peptides and a concomitant increase in their rate of rebinding. The presence of proteases, however, would cause DM-sensitive peptides dissociated from MHC II to be degraded before they have an opportunity to rebind, thus unmasking DM's repertoire-restricting activity.

TABLE 2

Post-source Decay Ions of the 3063 Da Species in the bCII(+)DM(+)Cath(+) Sample (See FIG. 1a) Comparison of Detected and Theoretical Ion Masses
peptide A: QTGEP$_{OH}$HGIAGFKGEQGPK$_{OH}$GEP$_{OH}$GPAGVQGAP$_{OH}$GPAG (SEQ ID NO: 8)
peptide B: QTGEPGIAGFK$_{OH}$HGEQGPKOHGEP$_{OH}$GPAGVQGAP$_{OH}$GPAG (SEQ ID NO: 9)

| | peptide A | | | peptide B | | |
|---|---|---|---|---|---|---|
| detected ions | ion type | theoretical | delta | ion type | theoretical | delta |
| 1161.12 | b12 | 1159.57 | −1.55 | b12 | 1159.57 | −1.55 |
| 1590.62 | y18 | 1591.77 | 1.15 | y18 | 1591.77 | 1.15 |
| 1646.83 | y19 | 1648.79 | 1.96 | y19 | 1648.79 | 1.96 |
| 1714.45 | b17 | 1714.84 | 0.39 | b17 | 1714.84 | 0.39 |
| 1770.65 | b18 | 1771.86 | 1.21 | b18 | 1771.86 | 1.21 |
| 1899.93 | b19 | 1900.90 | 0.97 | b19 | 1900.90 | 0.97 |
| 1960.19 | y22 | 1962.92 | 2.73 | y22 | 1962.92 | 2.73 |
| 2069.94 | b21 | 2070.97 | 1.03 | b21 | 2070.97 | 1.03 |
| 2237.62 | b23 | 2239.06 | 1.44 | b23 | 2239.06 | 1.44 |
| | y24 | 2238.08 | 0.46 | | | |
| 2293.83 | b24 | 2296.08 | 2.25 | b24 | 2296.08 | 2.25 |
| | y25 | 2295.10 | 1.27 | | | |
| 2520.26 | z28 | 2519.22 | −1.04 | | | |
| 2648.79 | b28 | 2651.27 | 2.48 | b28 | 2651.27 | 2.48 |
| | y29 | 2649.29 | 0.50 | y29 | 2649.29 | 0.50 |
| 2761.57 | z30 | 2761.31 | −0.26 | z30 | 2761.31 | −0.26 |
| 2818.57 | b30 | 2821.34 | 2.77 | b30 | 2821.34 | 2.77 |
| | z31 | 2818.33 | −0.24 | z31 | 2818.33 | −0.24 |
| 3045.97 | b33 | 3046.45 | 0.48 | b33 | 3046.45 | 0.48 |
| 3063.60 | parent | 3064.46 | 0.86 | parent | 3064.46 | 0.86 |

DISCUSSION OF EXAMPLES I-III

The present inventors have described a "minimalist" cell-free antigen processing system and exemplified such a system that comprises MHC class II, HLA-DM, and two cathepsins. Intriguingly, this system allows for processing of protein antigens and capture of immunodominant epitopes by the MHC molecules, and also provides direct evidence that DM plays a key role in establishing immunodominance. Unexpectedly, the DM-mediated enhancement of immunodominance occurs in synergy with lysosomal proteases.

Intrinsic stability of peptide/MHC II complexes (Lazarski et al., 2005) does not appear to be sufficient for determining immunodominance in the antigen/MHC H allele combinations tested by the present inventors, since many peptides not containing the antigens' immunodominant epitopes remained bound to HLA-DR1 in the absence of DM. DM prevented a variety of antigen-derived peptides from being efficiently captured by class II MHC molecules.

Figure 9:
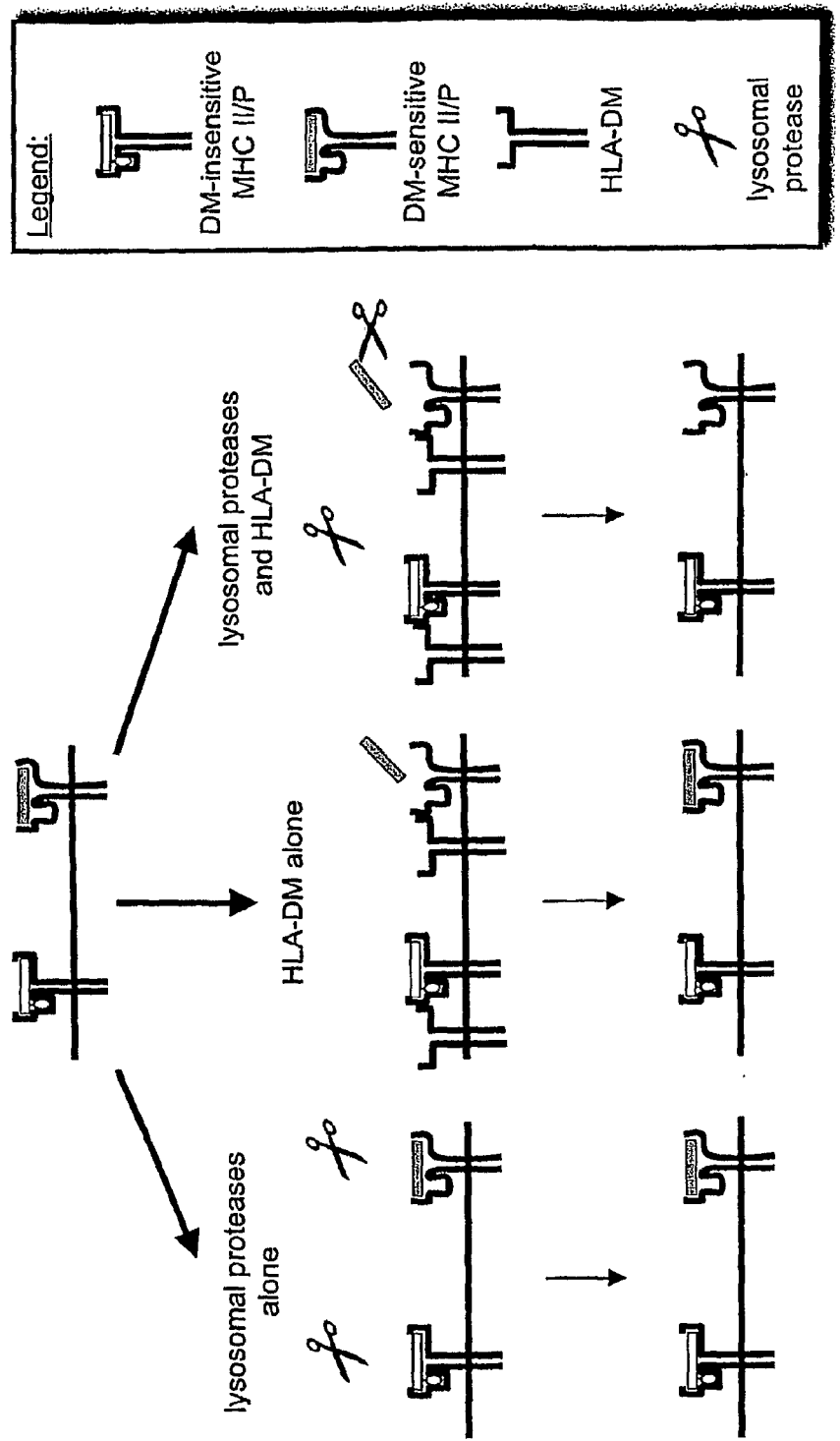
FIG. 9 presents a model for the cooperation between HLA-DM and lysosomal proteases in establishing immunodominance. The fate of two different peptide/class II MHC complexes (DM sensitive MHC II/P, empty P1 pocket; and DM insensitive), one sensitive to DM-induced dissociation and the other insensitive, are depicted under three different conditions: in the presence of lysosomal proteases alone, DM alone, and both DM and the lysosomal proteases.

While the invention is not limited or bound by any mechanistic explanation, the observation that lysosomal proteases enhance the ability of DM to restrict the repertoire of peptides captured by MHC H can be explained by the dual influence of DM on the peptide-MHC II interaction. While DM selectively enhances MHC II/peptide dissociation, depending on whether the peptide induces the MHC II to adopt a DM-sensitive conformation, it also globally enhances peptide-MHC II association by generating a peptide-receptive conformation (Chou et al., supra). The presence of DM causes both an increase in the dissociation rate of DM-sensitive peptides and a concomitant increase in their rate of re-binding. As a result, within a closed system (like the interior of an endosome), the proportion of DM-sensitive peptides that are bound to MHC II may not become dramatically lower by the action of DM alone. However, the presence of lysosomal proteases would unmask the repertoire-restricting activity of DM. Because DM-sensitive peptides have a higher rate of dissociation when DM is present, they will spend a greater proportion of time in the presence of DM in a free, unbound state in which they would be susceptible to degradation by the lysosomal proteases that are present in the environment. Thus, they will be proteolytically degraded before they have an opportunity to rebind MHC II. Conversely, peptides that are insensitive to DM-mediated dissociation remain bound to MHC II even in the presence of DM and are thus protected from proteolytic degradation. An illustration of this model for the cooperation between HLA-DM and lysosomal proteases is shown in FIG. 9.

A peptide may have an intrinsic rate of dissociation from MHC H that, while sufficiently low to allow for its co-immunoprecipitation with MHC H, is sufficiently high to lead to a high degree of exposure to proteolytic activity. Such is believed to be the case for HAY308A, which co-immunoprecipitates with HLA-DR1 even though it is efficiently eliminated by the addition of cathepsins alone. Such is presumably the case as well for the bCII-derived 3356 Da fragment.

In contrast, the bCII-derived peptides that require the action of both DM and lysosomal proteases for their removal presumably have a lower intrinsic (i.e., non-DM-mediated) dissociation rate so that they remain primarily in a MHC II-bound state when DM is absent, thus remaining protected from proteolytic degradation. In further contrast, the bCII-derived 3771 Da peptide, whose relative abundance is reduced by the presence of DM but is unaffected by the presence of the cathepsins, is presumably sensitive to DM-mediated removal but is resistant to degradation by cathepsins B and H.

For both antigens tested, the sequence heterogeneity of the antigen-derived peptides captured by HLA-DR1 in the presence of DM and cathepsins appeared to be extremely low. Only six species were detected in the reaction containing rHA1, and they most likely only represent three distinct peptides due to the presence of methionine-oxidized forms of each peptide. Although the sequence of only one of the mass species detected was reliably established through post-source decay (PSD) fragmentation, all of them are consistent in mass to peptide fragments of rHA1 containing the immunodominant HA306-318 epitope. Similarly for bCII, although the sequence of only one of the species in the sample derived from the reaction containing DM and cathepsins was reliably identified through PSD fragmentation, almost all of the other species in the sample are consistent in mass with the expected PTM variants of that peptide. This suggests that, at least for these antigen:MHC allele combinations, a limitation in the repertoire of TCR specificities that is available in the periphery may not need to be invoked as a crucial determinant of immunodominance. HLA-DR1 is an MHC II allele that is highly susceptible to DM-induced complex dissociation. Not all MHC II alleles are equally sensitive to DM (Koonce, C H et al., *J. Immunol.* 170:3751-61 (2003); Bikoff, E K et al., *J. Immunol.* 166:5087-5098 (2001); Wolf, P R et al., *Eur J Immunol.* 28:2605-18 (1998)), as structural differences among them promote different levels of DM resistance (Chou et al., supra). Immunodominance in those cases may be controlled by other mechanisms.

The approach taken in the present Examples serves as a model for the details of antigen processing. The cooperation between HLA-DM and lysosomal proteases in establishing immunodominance would have been extremely difficult, if not impossible, to demonstrate in studies utilizing living antigen-presenting cells. The present invention provides a tool to examine the sequence of events in binding of proteins vs. peptides to newly synthesized MHC H during antigen processing, and can help to test which specific lysosomal proteases are required for the proper processing of a given antigen. Furthermore, given the ability of this system to selectively capture the known immunodominant epitopes of well-characterized antigens, it is useful for identifying de novo the immunodominant epitopes of novel antigens.

Immunodominant epitope identification is the critical step in any rational design of antigen-specific immunotherapeutics. Current peptide screening assays are extremely tedious, uneconomical and generate false positive results because of their reliance on the ability of peptides to form stable complexes with MHC proteins while ignoring the editing function of DM. In addition, since these methods utilize chemically synthesized peptides, they do not account for post-translational modifications that may be present on the parent protein (Herzog, J et al., *Proc Natl Acad Sci USA* 102:7928-33 (2005)). In contrast, the present invention that utilizes the whole protein antigen allows addresses the presence of post-translational modifications, as is demonstrated by the results with type II collagen. Thus, the "minimalist" approach of the present invention can readily be expanded to a high-throughput system for efficient identification of "physiological" candidates for immunodominant epitopes within a large array of antigen/MHC II allele combinations. This is particularly useful for antigens of microorganisms or viruses responsible for emerging infectious diseases.

The references and sequence accession numbers cited herein are all incorporated by reference herein, whether specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

What is claimed is:

1. A method for producing an isolated or purified complex of an MHC class II restricted peptide from a polypeptide of interest, comprising:
   (a) optionally, denaturing the polypeptide of interest to produce a denatured polypeptide;
   (b) incubating the polypeptide or optionally denatured polypeptide in the presence of
      (i) a soluble human MHC class II protein or an active homologue thereof from another mammalian species; and
      (ii) soluble human HLA-DM protein or an active homologue thereof from another mammalian species;
   such that the polypeptide or optionally denatured polypeptide binds to the peptide binding groove of the MHC class II protein, forming a complex with said class II protein;

(c) proteolytically digesting exposed regions of said polypeptide or optionally denatured polypeptide so that a peptide of about 10 to about 26 amino acid residues remains bound to the peptide binding groove of said MHC class II protein, thereby producing said complex; and (d) further isolating or purifying said complex, thereby producing said isolated or purified complex of said MHC class II restricted peptide from said polypeptide of interest.

2. A method for producing an isolated MHC class II restricted peptide from a polypeptide of interest, comprising producing the complex in accordance with the method of claim 1, and further comprising the step of eluting or otherwise removing said peptide from said complex and isolating said peptide, thereby producing the isolated MHC class II restricted peptide.

3. The method of claim 1, wherein the soluble human HLA-DM protein is used in step (b)(ii).

4. The method of claim 1, wherein the human MHC class II protein is the a DR, DP or DQ protein.

5. The method of claim 4, wherein the human class II MHC protein is a DR protein.

6. The method of claim 5, wherein the human class II MHC protein is DR1.

7. The method of claim 1, wherein, in step (c), the proteolytic digestion is accomplished by a mixture of at least two proteinases.

8. The method of claim 7, wherein the at least two proteinases are cathepsins that occur naturally in mammalian endo/lysosomes.

9. The method of claim 8 wherein the at least two cathepsins comprise cathepsin B, cathepsin H, cathepsin S or cathepsin L.

10. The method of claim 9, wherein the at least two cathepsins are cathepsin B and cathepsin H.

11. The method of any one of claims 1, 2, and 3-10, further comprising sequencing said MHC class II restricted peptide.

* * * * *